(12) United States Patent
Gerlach

(10) Patent No.: US 7,241,358 B2
(45) Date of Patent: Jul. 10, 2007

(54) METHOD AND DEVICE FOR PRODUCTION OF A NUMBER OF LAMINATES

(75) Inventor: Herbert Gerlach, Ponteranica (IT)

(73) Assignee: Korma, S.p.A. (IT)

( * ) Notice: Subject to any disclaimer, the term of this patent is extended or adjusted under 35 U.S.C. 154(b) by 0 days.

(21) Appl. No.: 10/701,149

(22) Filed: Nov. 4, 2003

(65) Prior Publication Data

US 2004/0137215 A1      Jul. 15, 2004

Related U.S. Application Data

(63) Continuation of application No. PCT/EP02/04907, filed on May 4, 2002.

(30) Foreign Application Priority Data

May 4, 2001    (DE)    ............................ 201 21 347 U

(51) Int. Cl.
B32B 37/12    (2006.01)
B32B 37/24    (2006.01)
B32B 38/00    (2006.01)

(52) U.S. Cl. ...................... 156/276; 156/269; 156/291; 156/324

(58) Field of Classification Search ................ 156/276, 156/290, 291, 324, 344, 146; 427/180, 197, 427/198, 207.1, 208.6, 208.2, 264, 265, 270, 427/271
See application file for complete search history.

(56) References Cited

U.S. PATENT DOCUMENTS

| | | | | |
|---|---|---|---|---|
| 3,682,738 A | * | 8/1972 | Smith | .......................... 156/283 |
| 3,890,926 A | * | 6/1975 | Teed | .......................... 118/325 |
| 4,557,852 A | * | 12/1985 | Schulz et al. | .......... 252/186.35 |
| 4,571,924 A | | 2/1986 | Bahrani | |
| 4,675,209 A | | 6/1987 | Pedigrew | |
| 4,715,918 A | * | 12/1987 | Lang | ......................... 156/273.1 |
| 4,851,069 A | * | 7/1989 | Packard et al. | ............. 156/284 |
| 5,118,376 A | * | 6/1992 | Pigneul et al. | ............. 156/219 |
| 5,415,717 A | * | 5/1995 | Perneborn | .................... 156/276 |
| 5,494,622 A | * | 2/1996 | Heath et al. | ................ 264/40.1 |
| 5,540,804 A | * | 7/1996 | Raterman | .................... 156/500 |
| 5,560,794 A | * | 10/1996 | Currie et al. | .............. 156/73.2 |
| 5,766,388 A | * | 6/1998 | Pelley et al. | ............... 156/62.6 |

(Continued)

FOREIGN PATENT DOCUMENTS

DE    100 13 958 A    9/2001

(Continued)

OTHER PUBLICATIONS

International Search Report, Sep. 6, 2002.

*Primary Examiner*—Melvin Mayes
(74) *Attorney, Agent, or Firm*—Alston & Bird LLP

(57) ABSTRACT

The present invention relates to a method for producing a laminate with at least one powder layer, wherein the powder layer is continuously produced. A binder 164 is applied at least in strips to a first layer 167. The binder 164 comes to lie crosswise to a direction of movement of the first layer 167 between powder layers that are separated from one another. A second layer 169 is continuously supplied to the first layer 167 so that the first layer 167 and the second layer 169 surround the powder layer 168. Furthermore, the invention relates to an apparatus for continuously producing a laminate.

14 Claims, 14 Drawing Sheets

U.S. PATENT DOCUMENTS

| | | | |
|---|---|---|---|
| 6,054,631 A * | 4/2000 | Gent | 604/367 |
| 6,139,912 A * | 10/2000 | Onuschak et al. | 427/180 |
| 6,531,025 B1 * | 3/2003 | Lender et al. | 156/277 |
| 6,663,949 B1 * | 12/2003 | Tanaka et al. | 428/323 |
| 2001/0006089 A1* | 7/2001 | Ando et al. | 156/206 |
| 2002/0013560 A1* | 1/2002 | Erspamer et al. | 604/381 |
| 2004/0166248 A1* | 8/2004 | Hu et al. | 427/553 |

FOREIGN PATENT DOCUMENTS

| | | | |
|---|---|---|---|
| EP | 0 497 072 A | | 8/1992 |
| WO | 95/03019 | * | 2/1995 |

\* cited by examiner

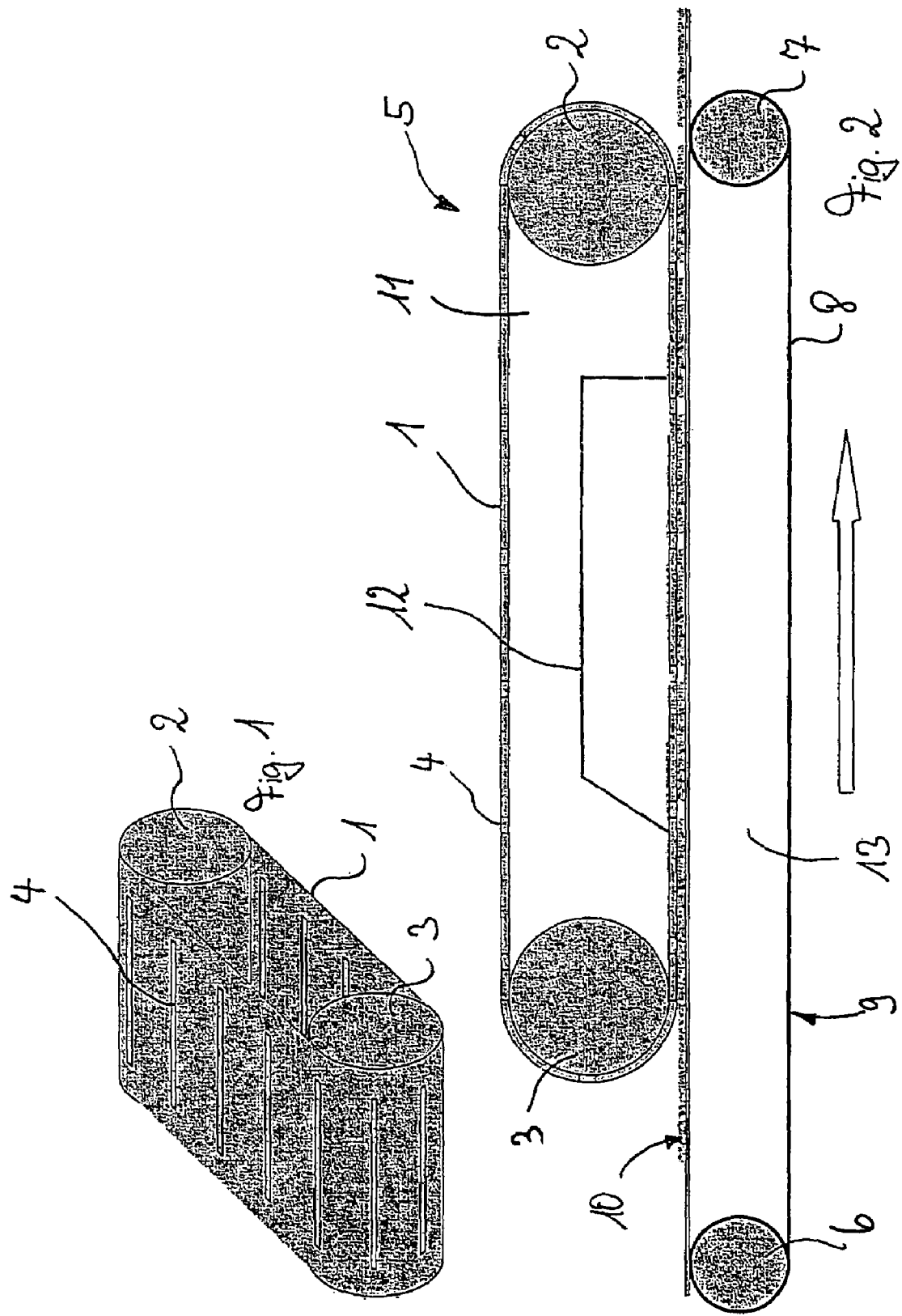

METHOD AND DEVICE FOR PRODUCTION OF A NUMBER OF LAMINATES

CROSS-REFERENCE TO RELATED APPLICATIONS

This application is a continuation of PCT Application No. PCT/EP02/04907, filed May 4, 2002, which claims priority from German Application No. 201 21 347.8, filed May 4, 2001, which are hereby incorporated herein in its entirety by reference.

FIELD AND BACKGROUND OF THE INVENTION

The invention relates to a method of producing a laminate with at least one powder layer, wherein a first layer is supplied to a second layer, and wherein at least the powder layer is applied to the first layer. In particular, an absorbent sheet is continuously produced by means of at least one layer of an absorbent material. Furthermore, an apparatus is made available for producing a laminate. The apparatus comprises at least one first feed device for supplying a first layer, a second feed device for supplying a second layer, and a feed device of an absorbent material for arranging at least one powder layer between the first and the second layer.

In the manufacturing field of hygienic products, the following art is known: EP 0 429 393 A2 discloses a method, wherein absorbent pads are produced for taking up body fluids in hygienic products. The method described therein permits producing in continuous operation any shape of absorbent pads without a time-consuming stacking of partial layers. For obtaining a profile in this process, excessive material is removed by suction and again returned. A cutting edge permits separating the thus-produced absorbent pads. EP 0 860 158 A1 discloses a method of producing an absorbent sheet, which includes an absorbent layer. A first layer, preferably of an airlaid material, receives by overlaying a second layer, preferably of the same material, with an absorbent material being arranged between these two layers. Both the first and second layers are continuously combined. Subsequently, this absorbent sheet is cut, with the cut edges of both the first and the second layer being spread apart for applying an adhesive as a binder to these end surfaces.

Proceeding from these references of the art, it is an object of the present invention to provide both a method and an apparatus for facilitating an automatic production method and for being simultaneously able to minimize both the time that is required for producing a finished product and the materials that are to be used.

SUMMARY OF THE INVENTION

The method of the invention for producing a laminate with at least one powder layer provides for supplying a first layer to a second layer and for applying at least the powder layer to the first layer. Before arranging the second layer on the powder layer and on the first layer, a portion of the powder layer is removed from the first layer, thus producing powder layers that are arranged separated from one another. Preferably, a binder is arranged at least in the form of strips between the separated powder layers for producing a transverse seal of the laminate.

A further development provides for applying by means of a first binder feed device, a first binder to the first layer in the longitudinal direction for producing a longitudinal seal, and by means of a second binder feed device a second binder to the second layer for producing a transverse seal, when the second binder comes into contact with the first layer.

It is preferred to use at least as one component of the powder layer a material that is capable of influencing at least a direct environment of the laminate. The direct environment may be gaseous, for example, air, and/or also liquid, for example, water. An influence may be exerted in many ways. Components may be released from the laminate, for example, perfumes or other substances, which may act upon one of more objects that surround the laminate. In this instance, the laminate has a dispensing function. The laminate is also capable of taking up, in particular absorbing or adsorbing liquids, particles, odors, or the like. One embodiment provides that at least one absorbent is used as ingredient of the powder layer, and that the laminate is produced as an absorbent sheet. A further embodiment provides that at least one odor influencing material is used as ingredient of the powder layer. Another embodiment provides that at least one detergent is used as ingredient of the powder layer. In addition, it is possible that the laminate has a plurality of functions, for example, releasing perfumes and detergents, or releasing detergents and taking up and storing certain liquid and gaseous components in the environment. In general, the laminate may simultaneously include a storage function, in particular an adsorbing function together with a dispensing function.

The powder in use may contain different ingredients. Likewise, the powder may have different grain sizes. For example, it is possible to use powders of different sizes, for example, from about the factor 5 to 10. They may be premixed and then be supplied to the first layer, or they may also be supplied in different regions of the first layer. A further embodiment provides for applying to the first layer with the powder layer or in the place thereof, a material having a different geometric configuration. This material may be, for example, fibrous materials, or even small spherical structures or hollow bodies.

In the following, the invention is described in greater detail by way of example with reference to an application as an absorbent sheet, without however limiting the following description to absorbent sheets. Rather, it is possible to apply all subsequent further developments, characteristics, and configurations to all other embodiments that have been described in the foregoing and will be described in the following. An absorbent sheet produced in accordance with the invention and comprising at least one absorbent layer provides that the absorbent sheet is continuously produced. A first layer is supplied to a second layer so that the first and second layers surround at least one absorbent containing layer. A binder is arranged at least in the shape of strips transversely to a direction of movement of the first layer, so as to be positioned between absorbent layers that are arranged in separated relationship for producing a transverse seal of the absorbent sheet.

A further development of the method provides that prior to applying the binder, a portion of the absorbent-containing layer is removed from the first layer. It is then possible to arrange, in particular apply the binder without disturbing binder particles to a thus-cleared section of the first layer. This facilitates joining, preferably bonding the first layer to the second layer. In addition, it is avoided that microcracks appear in the seal that is formed by this kind of joining, when tensile and/or shearing forces act upon a product subsequently made from the absorbent sheet. A tearing or opening of the per se closed product is avoided. Preferably, the binder is used to produce a transverse seal of the absorbent sheet. Moreover, there exists the possibility of continuously producing in addition to the transverse seal a longitudinal seal of the absorbent sheet. According to a further development, there also exists the possibility of producing both the transverse and the longitudinal seal by one and the same binder, for example, by applying it all over to the surface of the first layer. A further embodiment provides for furnishing a first metering unit for a transverse seal and a second metering unit for a longitudinal seal. This makes it possible to use for the respective seal different types and quantities of binders.

According to a further development, the binder is discontinuously supplied at least in part, preferably only in defined regions. This means, for example, that on the first layer, the binder is located only in a certain section. This section may form a transverse seal or also a longitudinal seal. It is likewise possible that one or more absorbent layers are at least covered or also interspersed with binders. To this end, it is possible to arrange the binder, for example, between different superposed absorbent-containing layers.

According to a further embodiment of the invention, at least one portion of the seal is mechanically produced, with the binder forming a mechanically acting engagement between the first and the second layer. A mechanical bonding is possible by means of carding, embossing, folding, or in any other way, with the material of the first layer, for example, engaging or adhering to the material of the second layer. To this end, one embodiment of the invention provides for a calender with a first and a second roll. The first roll is, for example, a smooth roll. The second roll is an opposite roll with a contoured surface, in particular an engraving roll. By means of the surface contour, the first and the second layer are interconnected at least in part in accordance with the contour. Preferably, at least one absorbent layer is completely sealed. The selection of the surface contour permits defining the geometry of the seal. A further development provides for using two rolls, which are both structured, in particular in such a manner that the one roll partially engages the other. With that, it is possible to form, for example, three-dimensional seals.

A further development provides that the first and/or the second layer include at least components that effect an adhesion under pressure and/or heat. These components may be, for example, adhesive fibers, which are included in at least one layer. Furthermore, it is possible that at least one of the layers that are to be combined includes bicomponent fibers, which enable a surface bonding. According to a further embodiment, a thin adhesive film extends between the first and the second layer. The adhesive film interconnects the two layers. The adhesive film may be fed in wide strips lengthwise or also crosswise for facilitating a longitudinal or transverse seal. If the first and second layers are advanced through a calender, they will be sealed in accordance with the surface structure and the arrangement of the adhesive.

A further embodiment provides that an adhesive is applied at least in part to the second layer, which is subsequently fed to the first layer carrying the absorbent layer. This makes it possible to use in particular a binder applicator that is in contact with the layer, and arranges thereon at least one strip of the binder. According to a further development, a transverse and/or longitudinal strip of the binder is applied to the first layer and/or the second layer. Subsequently, at least one absorbent layer is applied preferably to the binderfree region of the layer. In this manner, it is possible to realize in particular a transverse seal of the laminate.

The binder may be used, in particular applied to a layer in a wet or a dry state. Likewise in this manner, a binder can be applied, for example, by the rotary machine printing or the screen printing technique. Besides a solid strip of a binder, it is also possible to use bonding centers, bonding lines, or other geometries. Furthermore, the binder may be applied by means of a spraying process, for example, spiral spraying. Another embodiment provides for the use of a fiber spraying device. This spraying device permits positioning adhesive fibers between the first and the second layer for producing a seal. In particular for producing a seal, one may use a so-called "hot-melt" adhesive, which has in a heated state a higher viscosity that at room temperature, and which can therefore be applied in particular via jets. For example, it is possible to use a hot-melt adhesive on the basis of caoutchouc.

According to a further embodiment, it is possible to use as binder a fusible film. Preferably, the fusible film is at least vapor permeable, in particular fluid permeable. To this end, the fusible film may be perforated, for example, in a suitable mechanical or chemical way. Furthermore, it is possible to use a fusible web. Under pressure or heat, both the fusible web and the fusible film join the first layer to the second layer in desired locations.

For providing a seal, it is preferred to apply an adhesive in a quantity from about 1 to 7 $g/m^2$, in particular about 3 to 4 $g/m^2$. The applied powder, in particular the absorbent may be in an amount from about 30 $g/m^2$ to about 500 $g/m^2$, preferably from about 50 $g/m^2$ to 300 $g/m^2$.

An additional embodiment provides in an absorbent sheet not only for a mechanical sealing, but also a sealing by means of a different binder. For example, the transverse seal may be realized mechanically, and the lengthwise seal by applying an adhesive.

By arranging the binder in strips, preferably by applying it in strips crosswise to the direction of movement, a subsequent sealing becomes possible in a following step, without having to cut open the absorbent sheet one more time. Rather, it is possible to produce a thus-made absorbent sheet continuously and to subdivide it each time accordingly. Separate absorbent layers can be advanced to a subsequent processing step, for example, in a sealed, coherent state. For example, it is possible to wind or store the absorbent sheet as disclosed, in particular in WO98/57877, WO98/58864, WO99/59907, and WO00/53513. The contents of these publications are herewith incorporated by reference both with respect to depositing and stabilizing, and with respect to further processing and the marginal conditions and possibilities, that are to be observed in these processes. A further method of depositing the material is disclosed in WO98/18706, which is herewith also incorporated by reference as regards the depositing method and the parameters that are to be taken into account.

When depositing the absorbent sheet, it is preferred to see that folds are present only in regions that contain no absorbent layer. To this end, an absorbent layer is detectable, for example by means of a CCD camera, via a capacity measurement, or by means of a marking, which is furnished to the absorbent sheet mechanically or otherwise. For example, a sensor device supplies a signal to the depositing device, which causes, for example, a folding of the absorbent sheet by correspondingly reversing the direction of the deposit. When storing the absorbent sheet on a roll, it is preferred to operate with different tensions that act upon the absorbent sheet. The tensile forces are different and in particular dependent on the takeup speed as well as the respective loading state of the takeup drum. In this case, it is an object to avoid in particular a too loosely wound roll of the absorbent sheet.

A further variant of the method provides that the first and second layers are cut only after the absorbent layer has been totally sealed. This measure has the advantage that no absorbent material is able to escape, and that it is possible to process from the absorbent sheet in a continuous operation and according to predeterminable parameters, absorbent pads that are made ready for use in further processing. Furthermore, a preceding complete sealing makes it possible to process the absorbent sheet to a finished product in-line with a subsequent further processing step. On the other hand, it is also possible to store the absorbent sheet after its production and to make the required dimensions in a location of further processing. To this end, the absorbent sheet is advantageously provided with corresponding marking means, such as, dyed zones, metallic inlays or overlays, or similar detectable means, which can be actively or passively identified via a corresponding detecting device on the further processing apparatus, for example, for recognizing the position.

The above-described method makes it possible to deposit on the one hand the not yet separated, but already sealed absorbent layers. On the other hand, it makes it possible to store completely sealed and spaced absorbent layers, and to supply them subsequently to a further processing step, in which the sealed absorbent layers are separated from one another at least in part or also completely.

A further embodiment of the invention provides for depositing the individual, separated, and sealed absorbent layers and for supplying individual absorbent sheets to further processing. For example, while the individual absorbent sheets are jointly transported, they are already separated from one another in their packaging for transportation. It is possible to store, preferably stack the individual absorbent sheets in magazines such that they can be used in a further processing line, in particular directly from the magazines.

Another possibility in the production of absorbent sheets consists on the one hand in superposing not only one, but a plurality of absorbent layers. These layers may be of the same material or also of different materials. The latter makes it possible to achieve, for example, a purposeful fluid transportation within the absorbent layers by means of selecting the absorbent to be used and its behavior. Likewise, it is possible to separate a plurality of overlying absorbent layers from one another, for example, by another layer, an adhesive film, or the like. With the use of substances or other powder materials that are to be released from the laminate, it is likewise possible to provide a layered structure for special effects.

On the other hand, there exists the possibility of arranging adjacent absorbent layers in offset relationship in the transverse direction. This alternating arrangement permits producing on the one hand, for example, differently long absorbent sheets in side-by-side relationship. It is also possible that, for example, applicators for binders or the absorbent itself, as well as a suction device for excessive binder material operate more accurately, since adjacent contours are less affected in the course of processing.

According to another embodiment, it is also possible to form an absorbent sheet by a plurality of strips, which extend side by side and are not separated from one another. This makes it possible that, for example, one or more absorbent sheets are folded one on top of the other to thus form an absorbent pad. In this case, a seal is preferably realized by a folding plane.

Furthermore, the invention makes available an apparatus for continuously producing a laminate, in particular an absorbent sheet. The apparatus comprises at least one feed device for supplying a first layer, a second feed device for supplying a second layer, and a powder feed device, in particular a feed device of an absorbent, for arranging between the first layer and the second layer at least one powder layer, in particular an absorbent layer. The apparatus includes a material removing device, preferably in the form of a suction device for removing in particular by suction a powder, in particular absorbents in defined locations from the first layer, before feeding the second layer to the first layer for purposes of creating interruptions along a length of absorbents.

According to a further independent apparatus for continuously producing a laminate, in particular an absorbent sheet with at least one first feed device, a second feed device, and a powder feed device, in particular a feed device for absorbents, it is possible to arrange on the first layer at least one crossbar transverse of the direction of movement, for forming a boundary surface for a powder layer, in particular an absorbent that is to be applied. The crossbar is designed such as to keep a surface on the first layer free for forming a part of a transverse seal of the laminate, preferably the absorbent sheet.

Another, independently proposed apparatus for continuously producing a laminate, preferably an absorbent sheet, comprises at least one first feed device for feeding a first layer, a second feed device for feeding a second layer, and a powder feed device, preferably a feed device of absorbents for arranging between the first and the second layer at least one powder layer, preferably an absorbent layer. The powder feed device is followed by a binder feed device, which is adapted for applying discontinuously a binder to the material.

A further independent apparatus for continuously producing a laminate, preferably an absorbent sheet, comprises at least one feed device for a first layer, a second feed device for a second layer, and a powder feed device, which arranges a powder on the first layer at least before the second feed device advances the second layer to the first layer. A binder feed device for producing a transverse seal is arranged relative to the second feed device such that a binder can be applied to one side of the second layer, which is subsequently joined to one side of the first layer that receives a powder layer. As powder, one may use for example, an absorbent material.

Individually or jointly integrated in a production line for combining the first layer, the second layer, and at least the one powder layer, in particular the absorbent layer, the proposed apparatus can be used serially connected one time or several times. This integration enables a continuous production of the laminate, preferably an absorbent sheet. At the same time, one or more corresponding steps are taken, which subsequently result in that the powder layers of the laminate, or the absorbent layers of the absorbent sheet are sealed. In this manner, it is made possible to provide different production steps within a production line and apparatus. This permits saving equipment and time, which would otherwise be required for these steps in processing stations not integrated in the apparatus.

In the following, the invention is again described in greater detail with reference to an absorbent sheet, without however excluding the further above described applications, further developments, or characteristics, which contain other functions of an applied powder. Rather, it is possible to use the further developments that are described by means of an absorbent sheet, also for absorbent pads, absorbent cloths, scented pads, scented cloths, as well as for detergent pads or detergent cloths.

A further development provides that a depositing device follows, which receives, for example, absorbent layers that are interconnected but yet separated by complete seals. Preferably, the depositing device includes detection means, which permit distinguishing sections of the absorbent sheet with and without an absorbent layer. Depending on the quality of the absorbent sheet, this makes it possible to deposit it in a controlled manner.

Furthermore, the invention provides an absorbent sheet with at least one first layer, a second layer, and an absorbent layer, with the absorbent layer being arranged between the first and the second layer. A transverse seal of the absorbent sheet comprises a different binder than a longitudinal seal. According to a further development of the absorbent sheet, a force that is to be applied for destroying a transverse seal is greater than a force that needs to be applied in the case of a longitudinal seal, or vice versa. For example, a force from at least 20 $N/m^2$ to 25 $N/m^2$ will be needed for obtaining a destruction. If thermoplastics are used for providing seals, it will be advantageous to measure a heat-sealing strength, which is preferably in a range of more than 2 N/15 mm in a heat-sealing range from about 50° C. to 180° C. In particular, attempts are made to reach values of more than 6 N/15 mm, preferably a maximum of more than 9 N/15 mm before a total destruction of the seal. As testing method, one may use, for example, the spring test, or also the top wave DTC.

Preferably, the absorbent sheet includes at least one marking means, which permits detecting, for example, a manufactured line, for example, a cut, a folding line, a start and/or end of an absorbent containing layer, a position indication of the absorbent sheet as a reference point for a further processing line, as well as others. One or more marking means may be arranged in the absorbent containing layer, in a seal, or also in one of the layers.

Furthermore, the invention provides for a suction device in an apparatus for continuously producing a laminate, in particular an absorbent sheet. The suction device is designed and constructed such that it defines at least one location for removing by suction the powder, preferably absorbent material on a first layer by way of opening or closing a suction component of the suction device.

Further advantageous configurations and developments of the laminate, usable powders, manufacturing methods, etc. are described in greater detail in the following. The described details and the characteristics that are given with respect to the individual devices as regards both production and materials in use, parameters, marginal conditions, structures, components, and their interaction, as well as explanations, can also be applied in general to other apparatus and methods of the invention, whether or not they have been described above or will be described in the following. In particular, they can be combined with the above or below described embodiments to additional advantageous further developments.

BRIEF DESCRIPTION OF THE DRAWINGS

In the drawing:

FIG. 1 shows a continuous belt that is provided with slots;

FIG. 2 shows the belt of FIG. 1 installed in a first apparatus for continuously producing an absorbent sheet;

DETAILED DESCRIPTION

Figure 3:
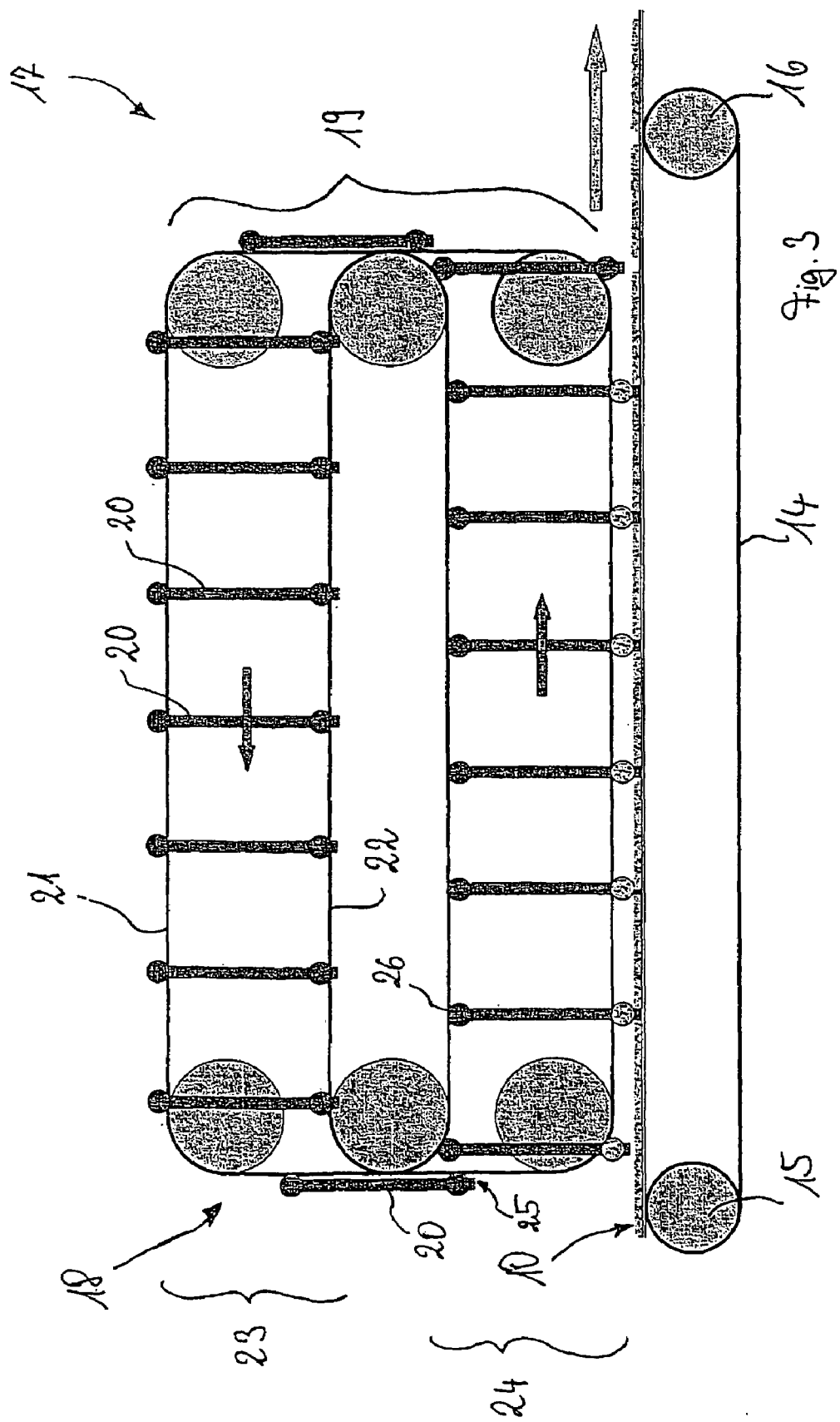
FIG. 3 shows a second apparatus for continuously producing an absorbent sheet.

The following explanations essentially relate to the embodiment of an absorbent sheet, without however being limited thereto. Rather, they deal with only a possible use of the laminate or the usable powder layers and their functions.

FIG. 1 illustrates a belt 1, which advances over a first roll 2 and a second roll 3. The belt 1 is provided with slots 4. The slots 4 extend transversely to a direction of movement of the belt 1. Preferably, the belt 1 is made of a plastic material, which is reinforced, for example, by means of fiber inlays. The slots 4 contained in the belt 1 extend through the belt 1. According to a further development, the material adjacent the slot 4 in belt 1 is at least in part reinforced, so that no cracks develop, when tensions act upon the belt 1.

FIG. 2 illustrates a first apparatus 5 for producing an absorbent sheet as a laminate. The first apparatus 5 comprises the first roll 2, the second roll 3, and the belt 1, as are shown in FIG. 1. Furthermore, the first apparatus 5 comprises a third roll 6 and a fourth roll 7. A second belt 8 extends over the third roll 6 and fourth roll 7. Preferably, the second belt 8 is a screen belt. However, it may also have no openings, but a closed surface 9. The surface 9 of the second belt 8 continuously receives a layer, which in turn receives a powder layer, in the present embodiment an absorbent layer 10. Preferably, both the belt 1 and the second belt 8 move at the same speed, so that the absorbent layer 10 advances in the direction of the arrow. A hollow space 11 formed by the belt 1 as well as the first roll 2 and the second roll 3 is adapted for receiving a suction device 12. The suction device 12 is schematically indicated and may be realized by means of a box-type structure arranged in the hollow space 11. In the box-type structure, a pressure prevails, which is lower than, for example, the ambient pressure. It is therefore possible to remove by suction the material of the absorbent layer 10 that is arranged in the direct vicinity of the slots 4. To this end, the second belt 8 is preferably at least in part porous or otherwise air-permeable. According to a further embodiment, in a second hollow space 13 that is formed by the third roll 6, the fourth roll 7, and the second belt 8, an overpressure is applied at least in part, so that the material of the absorbent layer 10 that is to be removed by suction, also enters the suction device 12. However, the suction device 12 itself need not be arranged in the first hollow space 11. Instead, it may also be located in the second hollow space 13. Furthermore, there exists the possibility that the removal by suction occurs over a wider range, so that the slots 4 cover a longer distance through the suction device 12. This makes it possible to lift and permanently remove the material from the second belt 8, preferably with little pressures. According to a further development, which is here not described in greater detail, there exists the possibility of operating within the suction device with at least one pressure gradient. For example, as the slots 4 pass through the suction device 12, the pressure will increase or decrease. In this process, the decrease or increase of the pressure may occur suddenly. This is made possible, for example, by means of a pressure reducer as well as via different pressure connections on the suction device 12 itself.

FIG. 3 shows a second apparatus 17 for continuously producing an absorbent sheet as a laminate. A depositing belt 14 that extends over a first roll 15 and a second roll 16 continuously receives the absorbent layer 10. The second apparatus 17 includes a suction device 18, which is arranged above the depositing belt 14. The suction device 18 comprises a system of rolls 19, over which suction attachments 20 advance. The suction attachments 20 are interconnected via a guide system that comprises a first connection belt 21 and a second connection belt 22. Preferably, the respective spacing between suction attachments 20 is variable. Likewise, the first and second connection belts 21, 22 are realized such that they permit inserting additional suction attachments 20. The suction attachments are guided by means of the roll system 19 along an upper path 23 opposite to a direction of movement of the depositing belt 14. After being deflected by means of the roll system 19, the suction attachments 20 advance along a lower path 24 in the same direction as the direction of movement of the depositing belt 14. In so doing, a lower opening 25 of a suction attachment 20 comes to slowly approach the absorbent layer 10. The suction attachment 20 comprises, for example, a suction stub 26 arranged at an end opposite to the lower opening 25. The suction stub 26 connects to a vacuum unit not shown in greater detail. As a result of the slow approach of the lower opening 25 to the depositing belt 14, the material in the direct vicinity of the lower opening 25 is removed by suction. Preferably, the suction device 18 is arranged such the lower end 25 moves forward as far as the depositing belt 14. This ensures that the absorbent layer 10 is totally removed in this region. The extent of the removal by suction of the absorbent layer directly adjacent the lower opening 25 can be adjusted via different parameters. These include, for example, the circulation speed of both the depositing belt 14 and the system of rolls 19, an adjustment of the respective speeds (it is also possible to adjust a speed difference between the depositing belt 14 and the suction attachments 20), the configuration of the lower opening 25, for example, additional suction openings at least along the length of the suction attachment 20 that engages the absorbent layer 10, an air volume flow as well as a volume itself that is removed by suction, a gas permeability of the depositing belt 14, a preprocessing of the absorbent layer 10 (for example, same may be present as a loose powder of a different grain diameter consistency, as prebonded absorbent material, as well as, for example, in the form of interconnected grains, in particular bonded grains, preferably as a solidified layer). In the apparatus shown both in FIGS. 3 and 2, surfaces coming into direct contact with the absorbent layer 10 are made such that the absorbent layer 10 does not remain stuck to these surfaces, when these surfaces are cleared from the absorbent layer 10. This occurs, for example, by way of a corresponding selection of the material of the surface, a corresponding surface improvement, for example, in the form of a coating. In particular, it is attempted that in comparison with the absorbent layer 10, the tendency to adhesion of this surface is smaller than a strength and with that an integrity of the absorbent layer 10 on at least its surface, in particular also over the entire material cross section of the absorbent layer 10.

Figure 4:
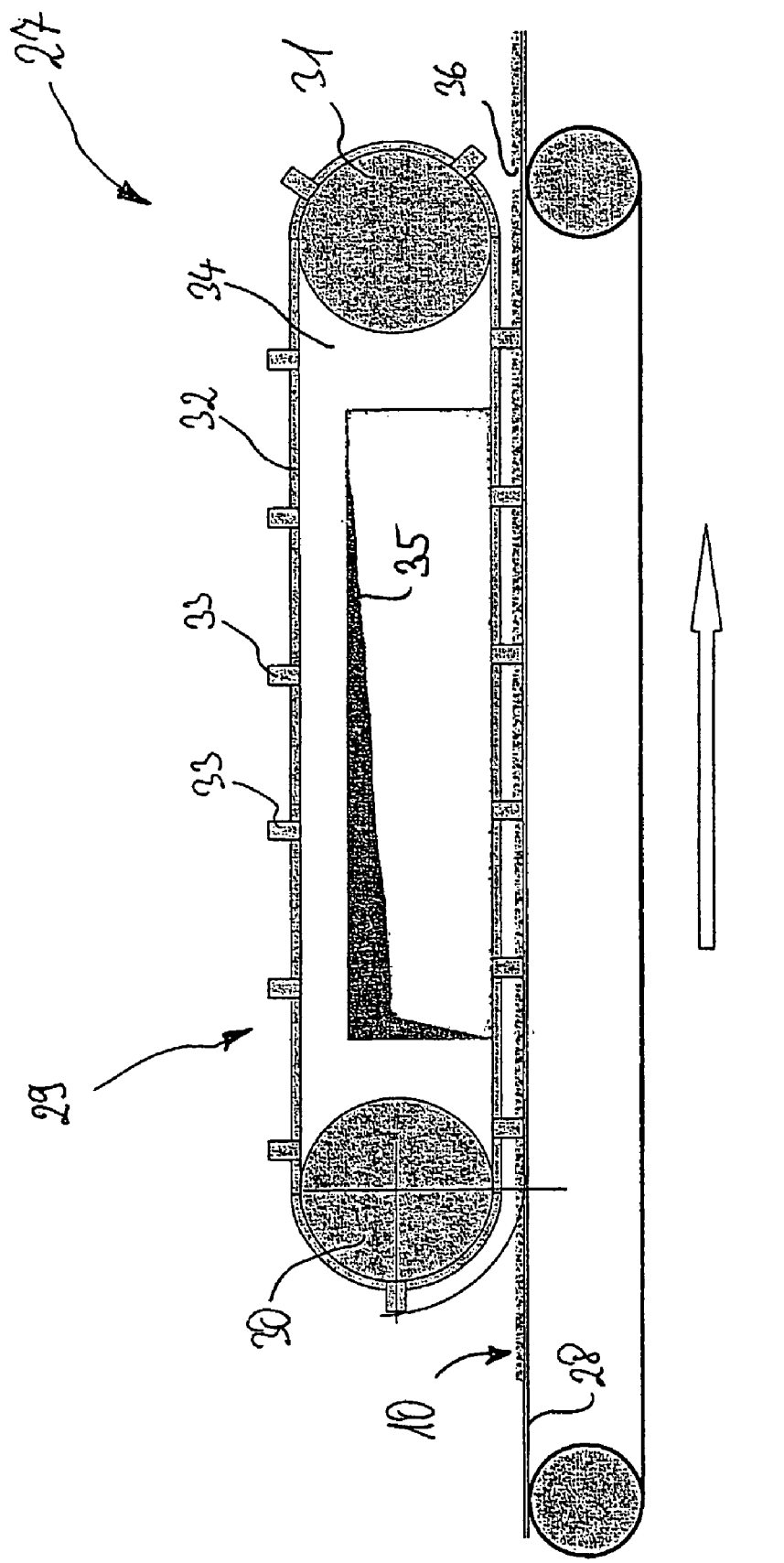
FIG. 4 shows a third apparatus for continuously producing an absorbent sheet.

FIG. 4 shows a third apparatus 27 for producing an absorbent sheet as a laminate. In the same way as the second apparatus 17 shown in FIG. 3, the apparatus 27 realizes the idea of a partial surface contact of a suction device with the absorbent layer 10. Preferably, this partial surface contact is limited to a suction device in the form of a suction attachment. FIG. 4 shows a configuration, in which the material of an absorbent layer 10 advances on a conveying belt 28 in the direction of the arrow. The third apparatus 27 also includes a circulating suction device 29. The suction device comprises a first conveying roll 30, a second conveying roll 31, and a guide belt 32. Inserted into the guide belt 32 are suction stubs 33, which are guided by the guide belt 32 over conveying rolls 30, 31. In this process, they come into contact with the absorbent layer 10. In an interior 34, a suction box 35 is arranged. Once the suction stubs 33 come into contact with the suction box 35, the material of the absorbent layer 10 located in the region of the suction stubs 33 is removed by suction. Advantageously, the suction box 35 is designed and constructed such that suction discontinues, before the suction stubs 33 are no longer in contact with the absorbent layer 10 or the conveying belt 28. This avoids that material of the absorbent layer 10 could still be removed laterally, or even fall back, when the suction stubs 33 are raised by advancing along the second conveying roll 31. Preferably, the suction stubs 33 of FIG. 4, and likewise, for example, in other technical further developments, devices engaging or adjoining the absorbent layer 10, have such geometry that an edge region 36 remains very largely undamaged. A corresponding configuration, for example, in conical, rounded, convex, tapered, or other fashion makes it possible to obtain an accurately defined edge region 36 within the absorbent layer 10 after completing the removal by suction.

Figure 5:
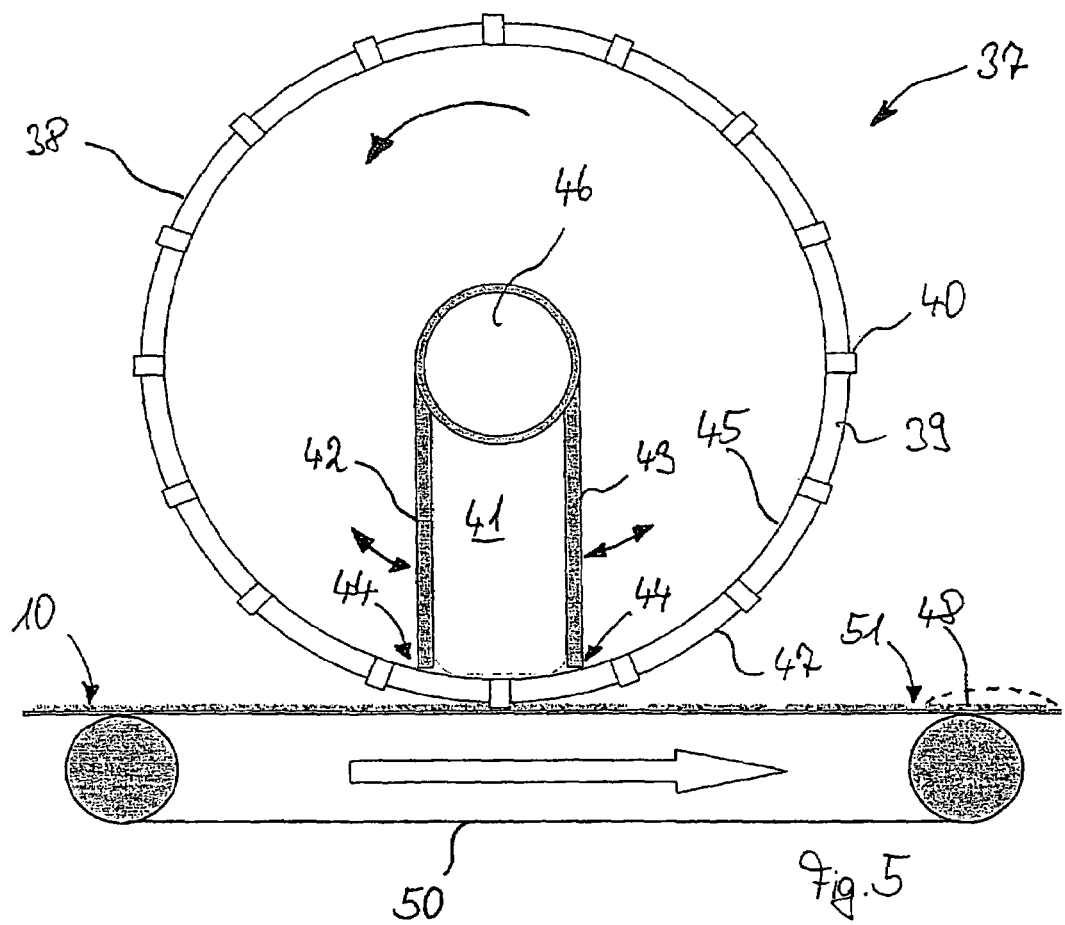
FIG. 5 shows a fourth apparatus for producing an absorbent sheet, with the device comprising a drum.

FIG. 5 shows a fourth apparatus 37 for producing an absorbent sheet as a laminate. In the place of a circulating belt, the fourth apparatus 37 comprises a drum 38 for removing material of the absorbent layer 10 by suction. The drum 38 is a hollow cylinder, whose outer edge 39 accommodates inserts 40. In the place of the inserts 40, the drum surface may also be provided with bores or correspondingly shaped projections. Preferably, a portion of the inserts 40 projects from the surface of the drum 38 and is thus able to engage the absorbent layer 10. The interior of the drum 38 accommodates a suction device 41. The suction device 41 comprises a first boundary 42 and a second boundary 43. At their respective ends 44, the boundaries 42, 43 sealingly engage an inner surface 45 of the drum 38. Via a discharge channel 46, the material removed by suction from the absorbent layer 10 reaches preferably a further processing station, where the material can be prepared and again returned to the process. Both the first boundary 42 and the second boundary 43 are preferably adjustable, whereby the removal by suction or the extent thereof is adjustable. Arrows indicate this adjustability. Preferably, the inserts 40 extend lengthwise, parallel to the axis of the drum 38.

According to a further development, they have a geometry of the type which enables a portion of the inserts 40 that comes first into contact with the absorbent layer 10 to cut out material from the absorbent layer 10. This will be especially advantageous, when the absorbent layer 10 already exhibits a certain strength on its surface, for example, by a preceding solidification as can be achieved by heating. Furthermore, an outer surface 47 of the drum 38 may be configured such that it has an embossing effect on the surface of the absorbent layer 10. For example, it is thus possible to shape the surface of the absorbent layer 10. This shape may be, for example, convex, concave, wavy, zigzagged, or otherwise, as is indicated by a dashed line along a section 48 of the absorbent layer 10. This first section 48 is separated from a following second section 49 in a direction transverse to the direction of movement of a conveying belt 50 that carries the absorbent layer 10. The still coherent absorbent layer 10 upstream of the drum 38 exhibits breaks 51 because of the suction. These breaks 51 may extend both in the longitudinal direction and in the direction transverse to the direction of movement of the belt 50. Preferably, the breaks 51 are realized such that no absorbent material is present on the belt 50 in these areas. As in the case of the foregoing apparatus, the conveying belt 50 may also be air-permeable. A further possibility consists in providing a multilayered belt 50, with each of these layers having a different porosity. In particular, the porosity decreases from the layer coming into direct contact with the absorbent layer 10 to the farthest removed layer. Likewise, the conveying belt 50 may be configured such that it possesses a type of carrier layer, which is in a position to ensure the necessary strength characteristics for a long lasting operation. Further layers on or around this carrier layer may have additional functions: for example, an improved acceptance of the absorbent layer, a satisfactory permeability, and a channel effect of air passing therethrough, etc.

Figure 6:
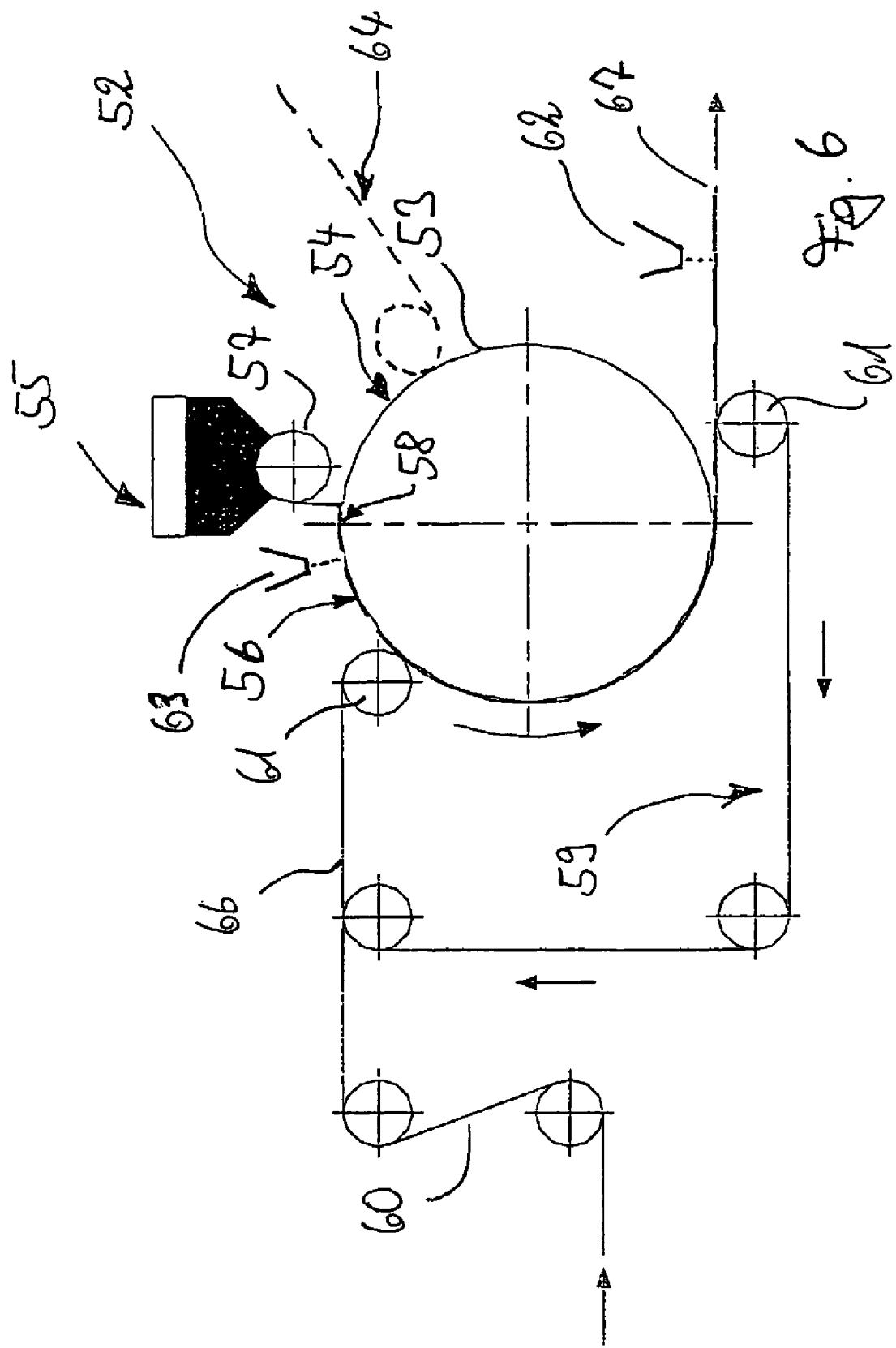
FIG. 6 shows a fifth apparatus with a drum, which has recesses in its surface.

FIG. 6 shows a fifth apparatus 52 for producing an absorbent sheet as a laminate. The fifth apparatus 52 comprises an application drum 53. A surface 54 of the application drum 53 may be smooth. In particular, it may also be roughened or, however, contain depressions. An absorbent material 56 is supplied to the surface 54 or the depressions via an absorbent layer feed device 55. The absorbent material may be fed continuously or discontinuously, so that preferably sections of absorbent material 56 develop, which are separated from one another. For example, an application roll 57 of the absorbent layer feed device 55 may be subdivided, so the absorbent material 56 undergoes a separation not only in the transverse direction, i.e., parallel to an axis of the application drum 53, but also in the circumferential direction thereof, for example, in the form of gaps. Preferably, the absorbent material 56 is applied at least in the direct vicinity of the highest point of the application drum 53. In particular, an application may also occur somewhat before this point 58. This ensures that the material is uniformly applied to the application drum 53. Preferably, not too far from the application of the absorbent material 56, a first layer 60 is supplied to the application drum 53 via a feed device 59, and brought into contact with the absorbent material. With the use of contact rolls 61 it is ensured that both the absorbent material 56 and the first layer remain in their position. Preferably via a binder feed device 62, a binder is applied to the first layer 60 such that the binder comes to lie crosswise to a direction of movement of the first layer 60 between disconnected layers of absorbent material. Subsequently thereto, a second layer not shown in greater detail is applied to the first layer 60 and the absorbent material 56. The thus produced absorbent sheet is transversely sealed in locations that have received a binder via the binder feed device 62.

A further development of this fifth apparatus 52 provides that a second binder feed device 63 follows the absorbent layer feed device 55. It is likewise possible to arrange the second binder feed device 63 in the direction of movement of the application drum 53 upstream of the absorbent layer feed device. Furthermore, a layer feed device 64 shown in phantom lines, supplies to a layer material 65 an absorbent material 56 or a binder material. Subsequently, the first feed device 59 supplies the second layer 66, so that the application drum 53 advances an absorbent sheet 67. Preferably, this sheet already includes transverse and longitudinal seals. To this end, for example, the second binder feed device 63 may be in a position to supply the binder not only in a discontinuous fashion, but rather permits in certain sections also a continuous supply of the binder material. If different binders are to be used for transverse and longitudinal seals, a binder feed device not shown in greater detail is provided in addition, for example, upstream or downstream of the second binder feed device 63. This allows separate binder feed devices, which can be operated in accordance with the type of binder with different pressures and temperatures.

Figure 7:
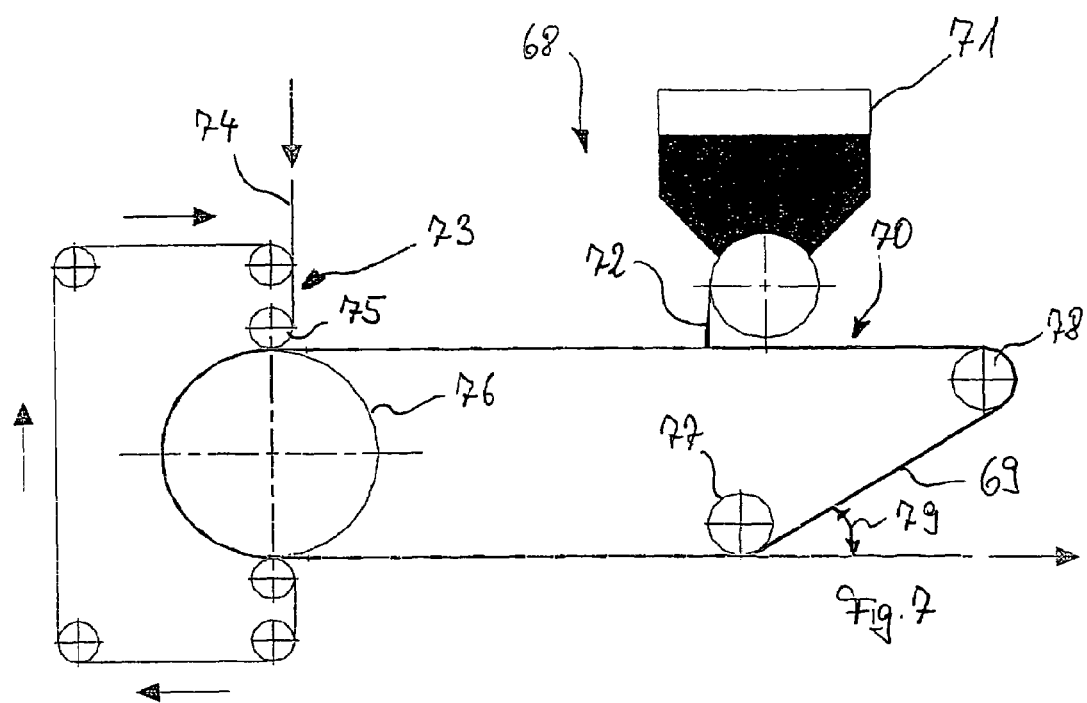
FIG. 7 shows a sixth apparatus with a belt, which has recesses.

FIG. 7 shows a sixth apparatus 68 for producing an absorbent sheet as a laminate. This apparatus uses a belt 69, which may have a roughened surface. A surface roughening results in that an absorbent 72 supplied by a feed device 71 is deposited continuously or, as shown, partially on the belt 69 and subjected there to a satisfactory adhesion. Furthermore, the belt 69 may contain recesses 70, which receive the absorbent material 72. Excessive material may be guided, for example, into the interior of the belt 69. To this end, the belt 69 may be constructed, for example, in the fashion of a mesh lattice, so that the absorbent 72 can settle only on correspondingly provided surfaces. It is likewise possible to remove excessive absorbent material 72 by suction. Downstream of the absorbent feed device 71 is a layer feed device 73. Via the layer feed device 73, it is possible to supply a first layer 74 to the belt 69. Contact rolls 75 see to it that the absorbent material 72 remains in position on the first layer, when being transferred from a large roll 76 toward a subsequent separation roll 77. As preferably in all solutions that have a direct contact between the absorbent material or absorbent layer or layers, it is preferred to configure the separation roll 77 such that a separation of a surface in contact with the foregoing does not lead to the destruction of the desired arrangement of the absorbent layer relative the one or the two layers. Preferably, an adjustment roll 78 follows the separation roll 77. Both the separation roll 77 and the adjustment roll 78 are adapted for displacement relative each other, in particular in such a manner that a separation angle 79 can be adjusted. An adequate tension in the belt 79 may be provided by means of equalization rolls, which are not shown in detail. A supply of binder material not shown in detail occurs, for example, after the first layer 74 leaves the separation roll 77.

Figure 8:
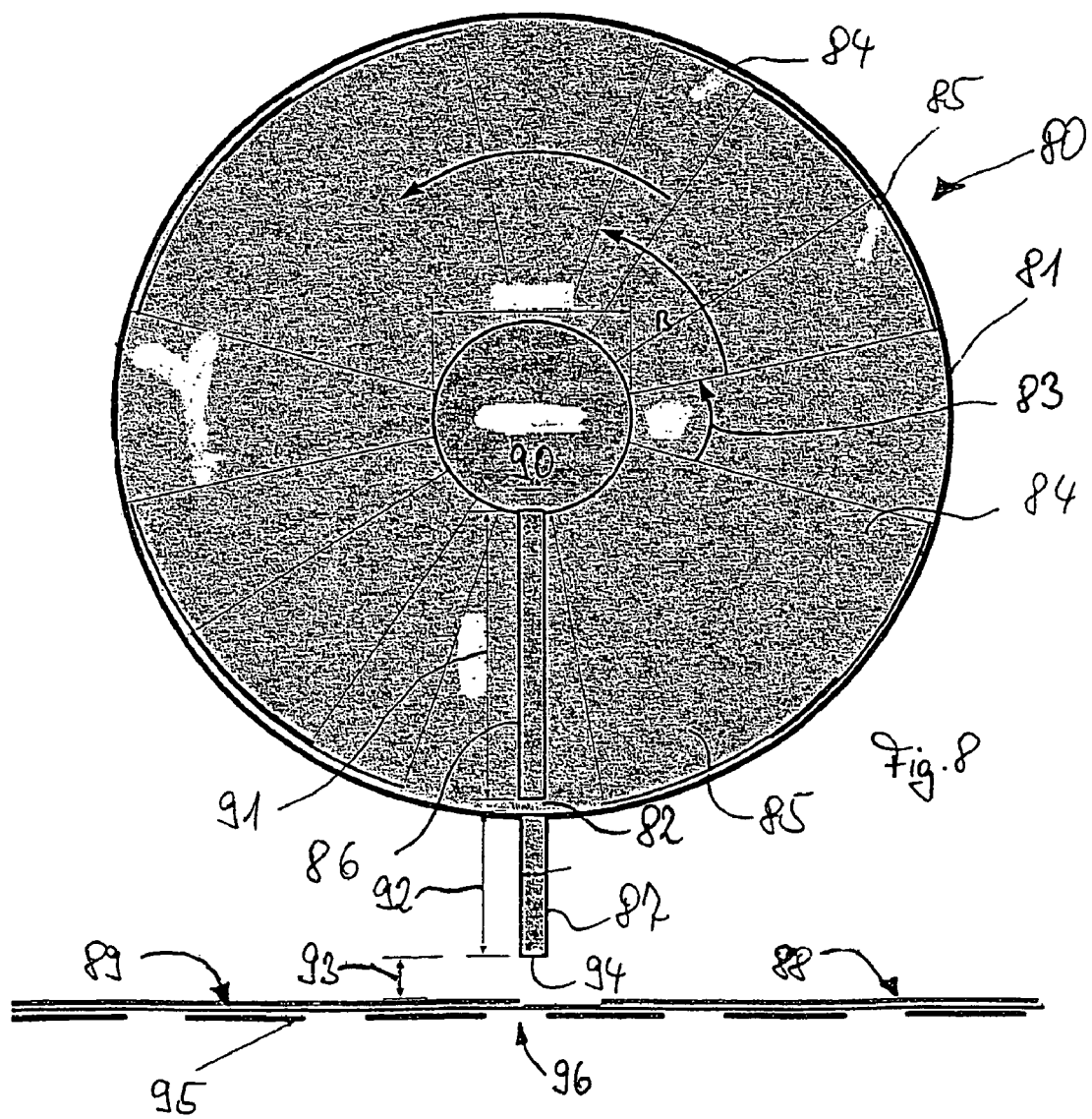
FIG. 8 shows a seventh apparatus with a hollow cylinder with variable suction openings.

FIG. 8 shows a preferred solution. Shown is a schematic view of a seventh apparatus 80 for producing an absorbent sheet as a laminate, with the apparatus comprising a hollow cylinder 81 with variable suction openings 82. The suction opening 82 extends over a sector angle 83. This sector angle 83 is adjustable by displacing first blocking segments 84 and second blocking segments 85, which are arranged in the hollow cylinder 81. Both the blocking segments 84 and the blocking segments 85 are interconnected, so that an inner cylinder is arranged for rotation in the hollow cylinder 81.

The inner cylinder with blocking and suction segments rotates, while the remaining elements are preferably stationary. By adjusting the first and second blocking segments 84, 85, it is possible to change the open sector angle 83. Along the open sector angle 83, a connection is established between a discharge component 86 and an intake component 87, which permit controlling the amount of an absorbent 88 that is to be removed by suction from a first layer 89. Furthermore, the kind of suction can be influenced, for example, via an applied pressure 90, via a length 91 of the discharge component, via a length 92 of the intake component 87, via a spacing 93 between the absorbent 88 and a suction opening 94 of intake component 87, their geometries, and other parameters. Furthermore, the suction behavior is defined by the geometry of the suction opening 94, by the development of a possible pulsation, by a configuration of a conveying belt 95 for a first layer 89, as well as other parameters. The conveying belt 95 comprises, as shown, openings 96. Preferably, it is a screen belt. The openings 96 facilitate a passage of air through the first layer 89 and thus a removal by suction of absorbent material 88. The apparatus 80 permits adjusting the suction. By varying, for example, the circumferential speed of hollow cylinder 81 as a function of the belt speed or segment adjustment in the inner cylinder, the apparatus 80 can be adapted to different lengths and widths of the absorbent material, as well as production speeds. The speed of the inner cylinder is determined from a reciprocal value, which is formed from the number of paired segments multiplied by an interval time. The interval time indicates the ratio of a length of absorbent material added by a length of an absorbent-free zone that follows in the direction of movement of the belt, to the speed of the belt.

Figure 9:
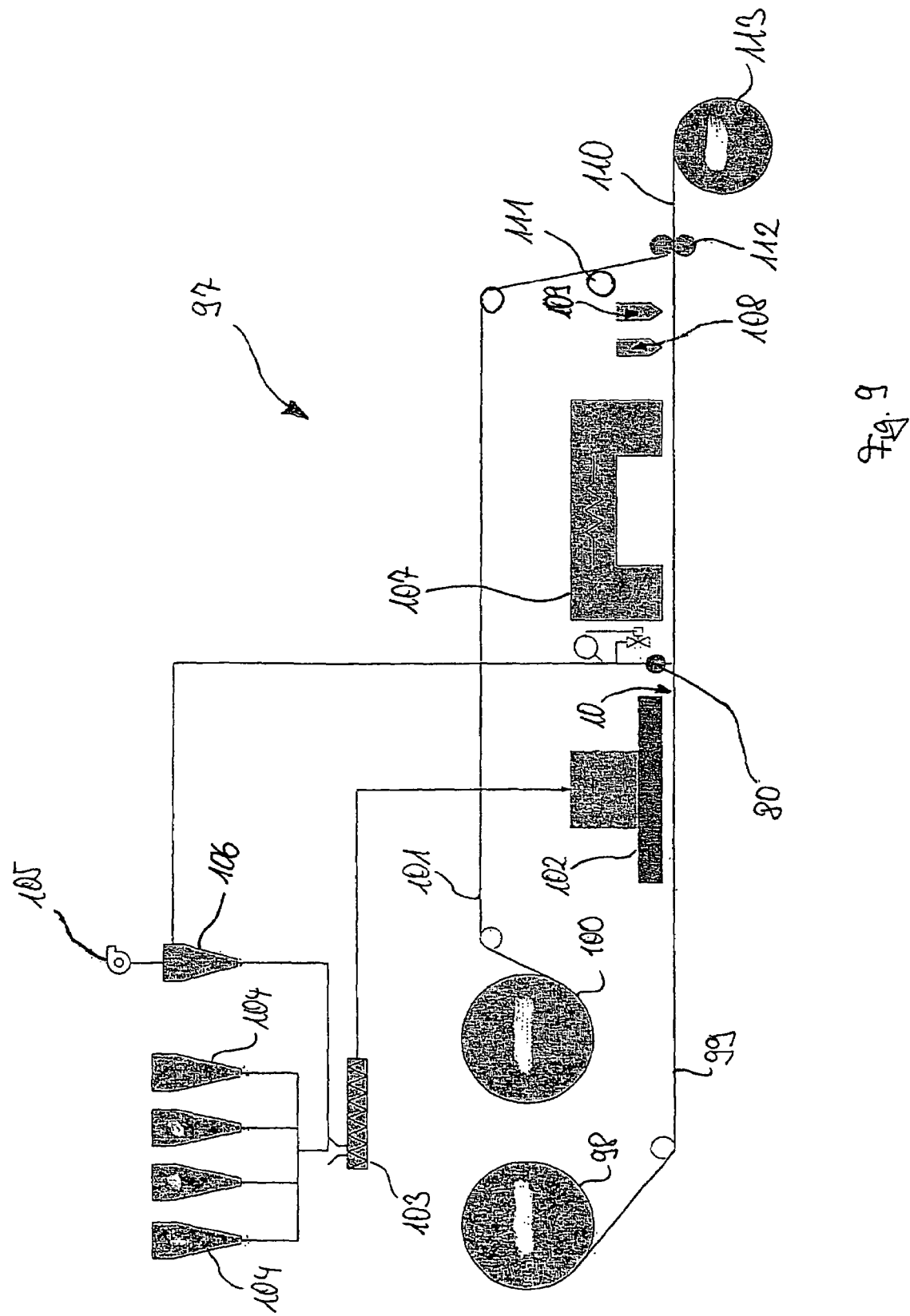
FIG. 9 shows an eighth apparatus, which includes, for example, a hollow cylinder of FIG. 8.

FIG. 9 shows by way of example an enlarged cutout view of an apparatus 97 for producing an absorbent sheet as a laminate. Into this apparatus 97, it is possible to integrate, for example, the seventh apparatus 80 of FIG. 8. From a first unwinding station 98, a first layer 99, and from second unwinding station 100, a second layer 101 are supplied to a further processing line. Furthermore, in the place of the first and second unwinding stations 98, 100, it is also possible to run an in-line process for producing the unwound layers. This means that the material of the first or second layer 99, 101 is produced directly before a further processing. A first layer 99 receives an absorbent layer 10 via an absorbent material feed device 102, which connects to a mixing unit 103. The mixing unit 103, for example, a rotary mixer, in turn connects to supply bins 104. The supply bins 104 store, for example, different materials for the absorbent layer, which are mixed according to a predeterminable formulation, and applied as absorbent layer 10 by means of the feed device 102. For example, the supply bins 104 may store, alone or also in blends, superabsorbents, cellulose, binders, additives, fragrances, zeolite, and fiber material. The supply bins 104 may also store further, normally usable materials alone or in blends. A further advantage of the arrangement of one or more supply bins is that the continuous process can proceed without interruption for refilling correspondingly suited material by switching the feed line from one supply bin to another. After applying the absorbent layer 10 to the first layer 99, same advance to the seventh apparatus 80. There, the absorbent material is removed from the first layer in selected areas. Besides a removal by suction, there also exist other possibilities, such as, for example, a mechanical stripping of a portion of the absorbent layer 10. To be able to adjust in the case of a removal by suction a uniform suction pressure, the latter is, for example, controlled. To this end, one may use a throttling system, in particular, also a bypass solution. The bypass solution is used to deliberately generate a partial airflow, which is used to facilitate the supply of powder to a cyclone 106. It is also possible to realize in a speed controlled manner a vacuum-generating unit 105, for example, a fan. According to one development, the absorbent material that is removed by suction is separated from the suction air current, for example, via a separator, which is illustrated in the present embodiment by the cyclone 106. After a corresponding preparation, the thus recovered absorbent material is again returned to the cycle.

After removing absorbent material by suction from the absorbent layer 10 according to the embodiment of FIG. 9, the first layer 99 advances into a heating zone 107. For example, in the case of feeding a polymer material to the absorbent material 72, the there occurring heat transfer causes the absorbent material to soften, or to even melt. As a result, the grains of the absorbent material adhere to one another and form a stable layer of the absorbent material on the first layer 99. Furthermore, a corresponding heating moreover results in that the absorbent layer adheres to the surface of the first layer 99. In a modification of the apparatus 97 not shown in greater detail, a heating occurs in a heating zone 107 before the absorbent layer 10 is in part removed from the first layer 99. Preferably, the removal is caused in particular by means of mechanical action. To this end, for example, a correspondingly shaped roll or surface, which is guided, for example, by a revolving belt, cuts into the absorbent layer 10, and removes it in a desired area. A precured absorbent layer 10 has the advantage that forces, which act upon this layer, may be greater, before an unwanted disturbance occurs in the remaining areas of the absorbent layer.

In FIG. 9, the heating zone 107 is followed by a first binder feed device 108 and a second binder feed device 109. In the direction of movement of the first layer 99, the first binder feed device 108 applies a first binder, which leads in the further course because of its transversal arrangement to a longitudinal seal between the first and the second layer 99, 101. To this end, the first binder is applied in a space that is preferably free from absorbent material. The second binder feed device 109 applies a second binder to the first layer 99. The second binder is applied in such a manner that it leads to a transverse seal in an absorbent sheet 110. Both the first and the second binder may be applied by spraying, by a direct contact of an application head, or otherwise. A further possibility of applying the second binder consists in wetting the second layer 101 accordingly. For example, this may occur with a roll as a third binder feed device 111, which is provided with application surfaces. According to a further embodiment, the surface of the third binder feed device 111 includes elevations that are wetted with a binder at a rotational speed, which is synchronized with the advance of the first layer 99. Subsequently, the binder is applied to the surface of the second layer 101. In particular with this solution, it is made possible that the third binder feed device 111 is in constant contact with the second layer 101.

After applying one or the other binder, the first layer 99 and the second layer 101 are laminated with the absorbent layer 10 arranged between them to an absorbent sheet 110 by means of a pressure unit 112, in this instance a calender. The calender may be structured at least on one roll surface. The structure has, for example, the task to shape and/or seal the absorbent layers. According to the illustrated embodiment, the absorbent sheet 110 becomes storable by way of a takeup unit 113. Furthermore, a further development makes it possible to advance the absorbent sheet 110 directly to a further processing apparatus, in which the absorbent sheet is divided both lengthwise and crosswise into individual absorbent packets. The individual absorbent packets not shown in greater detail are used in products, such as, for example, hygienic articles, wipes, oil absorbing cloths, or others.

Figure 10:
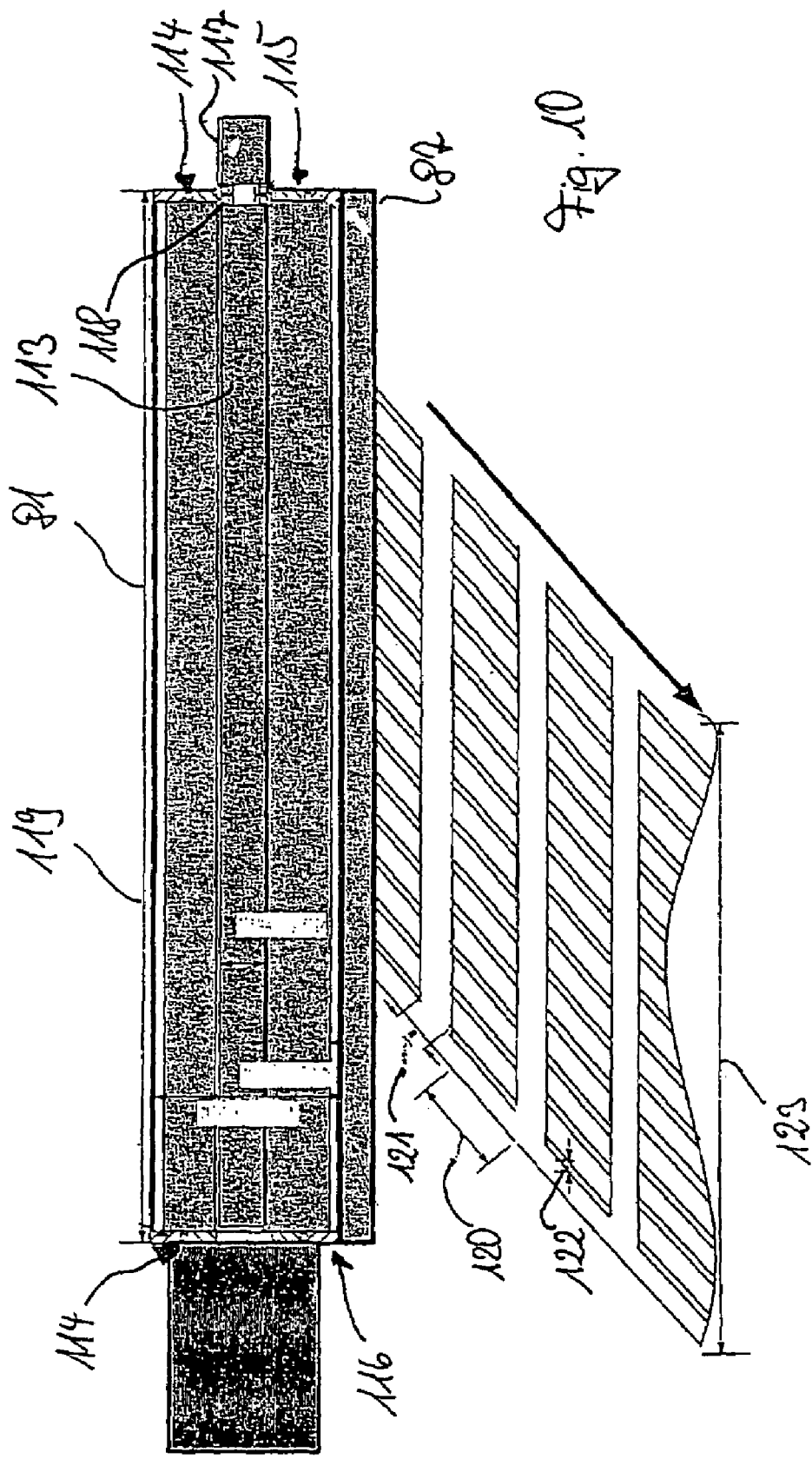
FIG. 10 is a sectional view of a hollow cylinder, as shown, for example, in FIG. 8.

FIG. 10 is a schematic, axially sectioned view of the hollow cylinder 81 of FIG. 8. For its inner hollow core 113, through which a vacuum is made available to intake 87, the hollow cylinder 81 comprises a bearing 114. For example, the bearing 114 is arranged, respectively, on a first end face 115 and a second end face 116. A connection 117 to a vacuum-generating unit not shown in greater detail is provided, for example, via a corotating rotary passageway 118. The rotary passageway 118 is made gastight, so that no leakage whatsoever will occur while transmitting the vacuum. In order that over a length 119 of the hollow cylinder the same vacuum is applied all over at the same time, the inner hollow core 113 preferably comprises valve-type fittings so that a minimum vacuum is uniformly applied after opening the intake and starting the removal of absorbent material. In this manner, it is possible to produce absorbent layers 10, which may have any desired length 120, for example, between 45 mm and 181 mm. It is easy to produce longer layers of absorbent material. A spacing 121 in the longitudinal direction between absorbent layers can be progressively adjusted. This spacing ranges preferably from 60 mm to 25 mm. A width 122 of the absorbent layers can be adjusted in any desired manner, and ranges, for example, from 6 mm to 50 mm. Exact dimensions of the absorbent layers are dependent on different parameters. They are influenced on the one hand by the later end use of the product, the production speed, the used materials, as well as their thickness that is to be applied. For example, it is possible to arrange absorbent layers continuously over a width 123 of the first layer of 100 cm and larger. The indicated dimensions can also be achieved by means of the other apparatus and methods.

Figure 11:
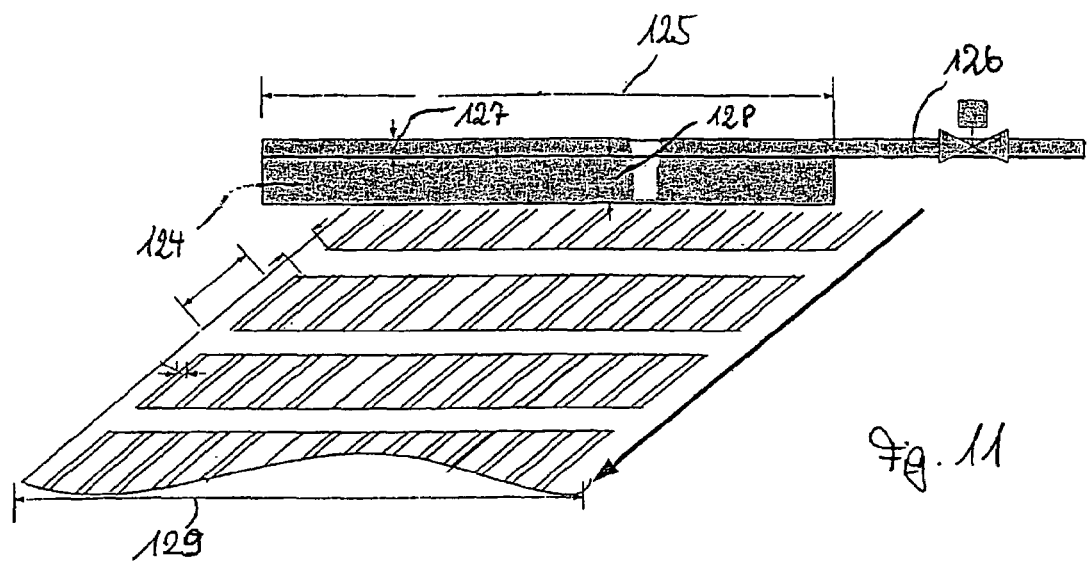
FIG. 11 shows a suction channel, as can be used, for example in a device of FIG. 9.

FIG. 11 shows a further embodiment of a suction device, which uses a channel 124 that can be employed in an apparatus of FIG. 9. The suction channel 124, which has, for example, a length from 200 to 800 mm, is arranged above a first layer, and connects to a vacuum feed line 126. The vacuum feed line 126 has, for example, a diameter 127. The suction channel 124 in turn has a height 128. Preferably, the height 128 of the suction channel 124 is greater by a factor from 1.5 to preferably 4 than the diameter 127. The length 125 of the suction channel 124 in turn is longer, preferably by the factor 1.1, in particular 1.3 and higher, than the width 129 of the used first layer. The pressure prevailing in the suction channel 124 or via the vacuum feed line 126, is likewise controlled via a magnetic valve. This valve permits a fast opening or closing in a range of less than 5 seconds, in particular in a range from 50 ms to 4 ms.

Figure 12:
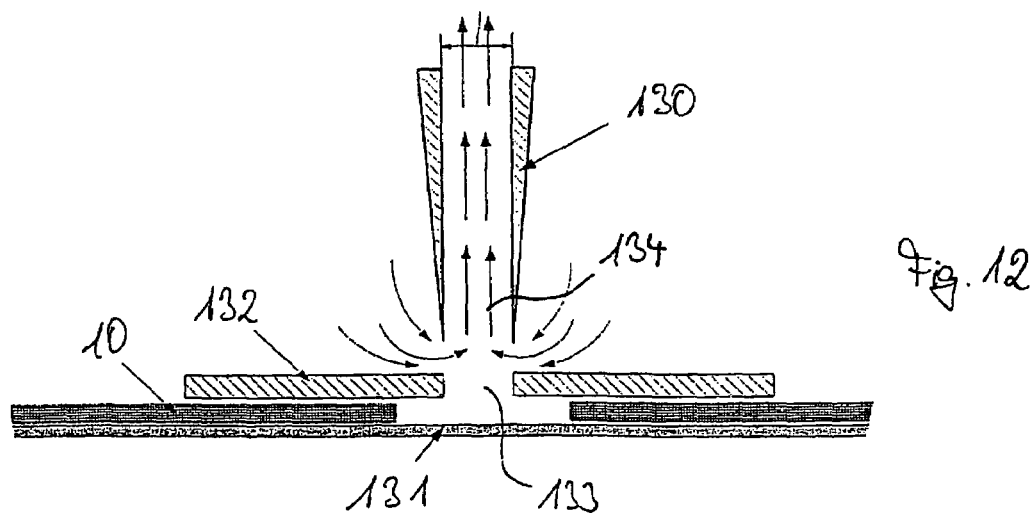
FIG. 12 is a schematic view of an embodiment of a suction intake opening.

FIG. 12 is a schematic view of an embodiment of a suction opening 130. In the illustrated embodiment, a mask 132 is arranged above the absorbent layer 10, and thus above a first layer 131. Preferably, the mask forms a diaphragm, and prevents with its gap 133 that in the course of a suction, more material of the absorbent layer 10 is removed than necessary. The mask permits an exact separation between zones that are to be cleared by suction, and zones that remain untouched, in particular by the absence of a false flow resulting from an airflow of the environment. Furthermore, the mask 132 allows in a further embodiment that a certain pressure, for example, a vacuum or a mechanical pressure is exerted on the absorbent layer 10. Preferably, the gap 133 is somewhat smaller than the suction opening 130. In other embodiments, however, the gap 133 may also be larger. The suction opening 130 in turn may be made conical with an inside diameter 134 that can increase or decrease in the direction of the flow. This depends on whether or not it is intended to obtain a high or a low suction speed directly on the absorbent layer 10.

Figure 13:
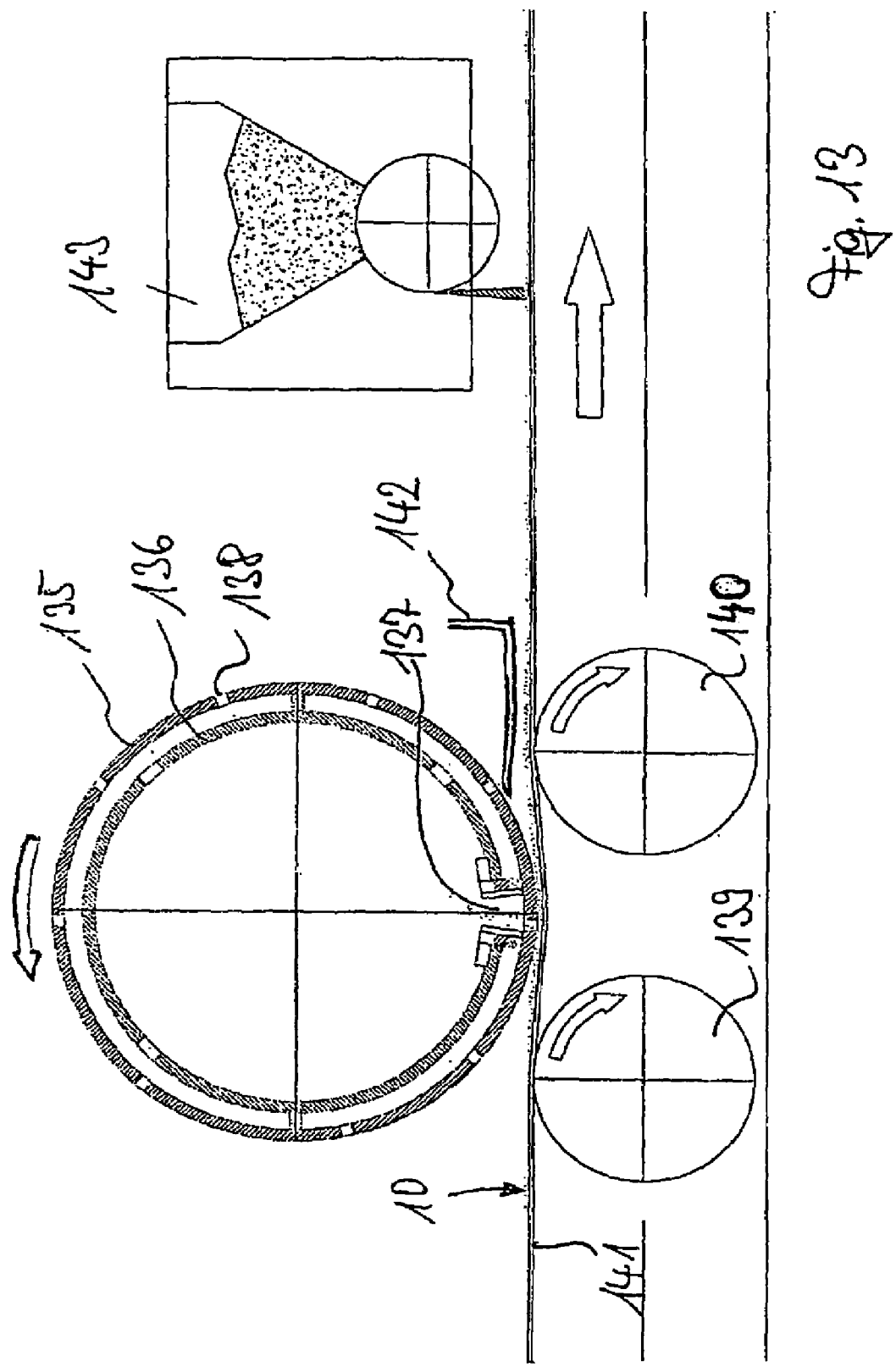
FIG. 13 shows a ninth apparatus for producing an absorbent sheet.

FIG. 13 shows a further device for producing an absorbent sheet. This apparatus employs again a hollow cylinder 135, which accommodates an inner hollow cylinder 136. The inner hollow cylinder 136 comprises a suction channel 137, through which a vacuum can be applied to suction openings 138 of the hollow cylinder 135. To this end, the hollow cylinder 135 rotates about the inner hollow cylinder 136. Arranged in facing relationship with the hollow cylinder 135 are a first opposite roll 139 and a second opposite roll 140. Preferably, the hollow cylinder 135, the first opposite roll 139, and the second opposite roll 140 are arranged such that a first layer 141 that carries an absorbent layer 10, is displaced toward the opposite rolls 139, 149. This results in a force of pressure on the absorbent layer 10, whereby preferably only material is removed from the absorbent layer 10, which is arranged in direct facing relationship with a suction opening 138. The pressure that is exerted by the position of the hollow cylinder 135 relative the two opposite rolls 139, 140, is adjustable, preferably by changing the position of at least one of these three rolls. To avoid that absorbent material adhering to a surface of the hollow cylinder 135 is entrained by same, a cleaning device 142 is arranged on the hollow cylinder 135. This device permits cleaning the surface of the hollow cylinder 135, for example, by means of mechanical action, by compressed air, or other possibilities. The dropping material is collected and removed by the cleaning device 142. Moreover, the surface of the hollow cylinder 135 may be coated, so that a tendency to adhesion, in particular vis-a-vis grainy materials is extremely reduced. Downstream of the cleaning device 142 is a binder feed device 143, which permits applying a binder to the first layer 141 in part or all over its surface.

Figure 14:
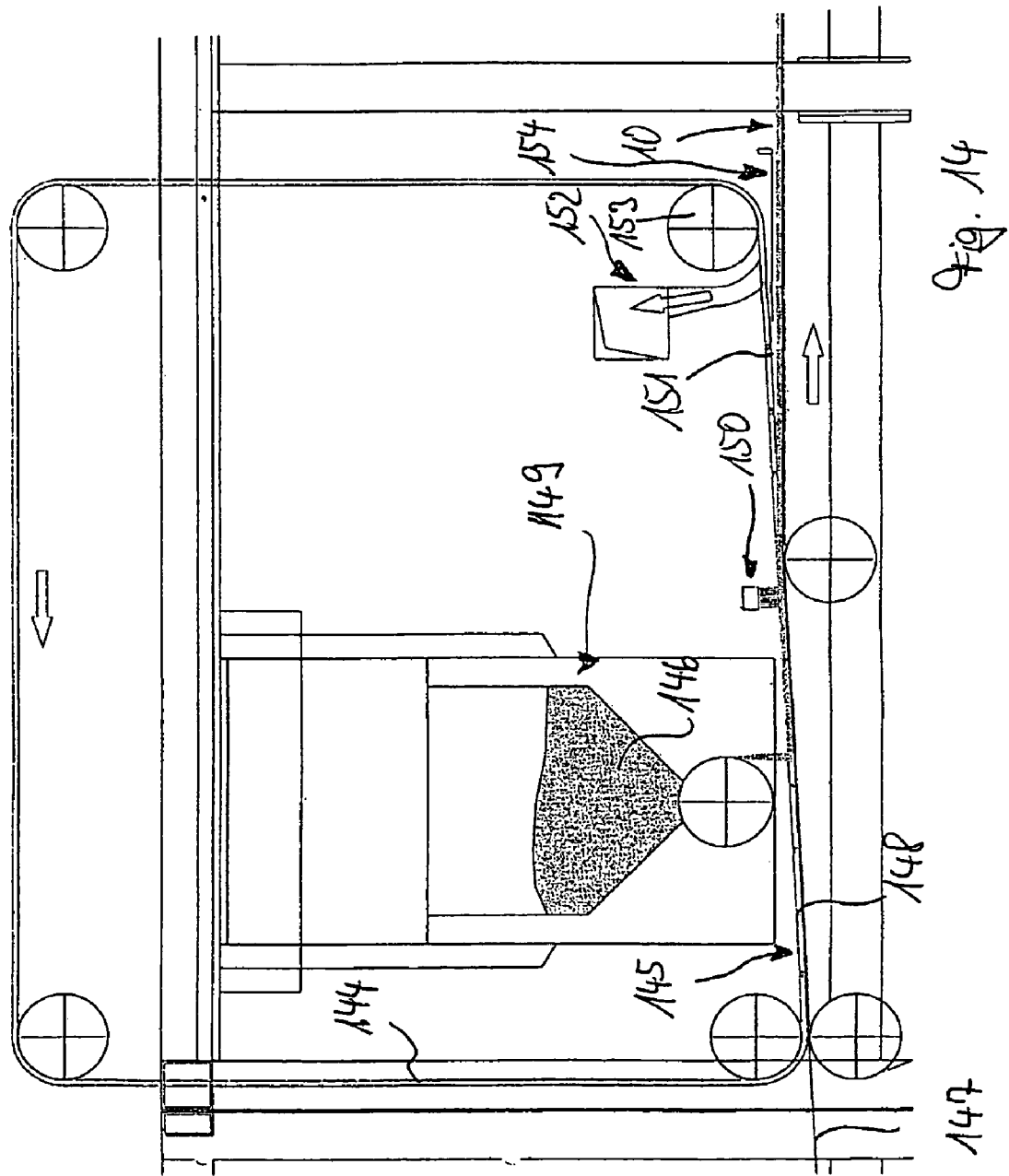
FIG. 14 shows a tenth apparatus for producing an absorbent sheet.

FIG. 14 shows a further embodiment of an apparatus for producing an absorbent sheet. In the case of this apparatus it is shown by way of example that it is also possible to revamp an existing production line with an apparatus of this type for producing an absorbent sheet and in particular for a partial application of absorbent material. As schematically indicated, the apparatus is compactly accommodated in a frame structure. In accordance with correspondingly available space within a production line, it is therefore possible to install the apparatus as a module at a later date. Via a revolving belt 144, which has openings 145, an absorbent material 146 is applied to a first layer 147. The belt 144 is provided with crossbars 148, which are in contact with the first layer 147. The crossbars 148 partially cover the surface of the first layer 147. A feed device 149 distributes the absorbent material 146 via the belt 144 over the first layer 147. The material that comes to lie on the crossbars is distributed to a desired height by means of a spreading device 150, for example a brush, a wiper, or the like. Subsequently, the belt 144 is raised at a slight angle of inclination 151 from the first layer 147 and the absorbent layer 10 distributed thereon. The angle of inclination 151 is preferably from 5° to 35°. Thereafter, the belt 144 is freed from possibly adhering particles by means of a cleaning device 152. The cleaning device 152 may use, for example, suction or even ultrasound. To collect particles that drop from the belt 144, a collection device 154 is arranged in the region of a deflection 153. Moreover, one may compact the absorbent layer 10 in the present apparatus in the same way as is done in the above described apparatus, for example, by exerting pressure by means of rolls, or also by exerting pressure via the spreading device 150. A further possibility of compacting results from a corresponding vibratory compacting. A corresponding vibration can be generated, for example, by means of ultrasound.

Figure 15:
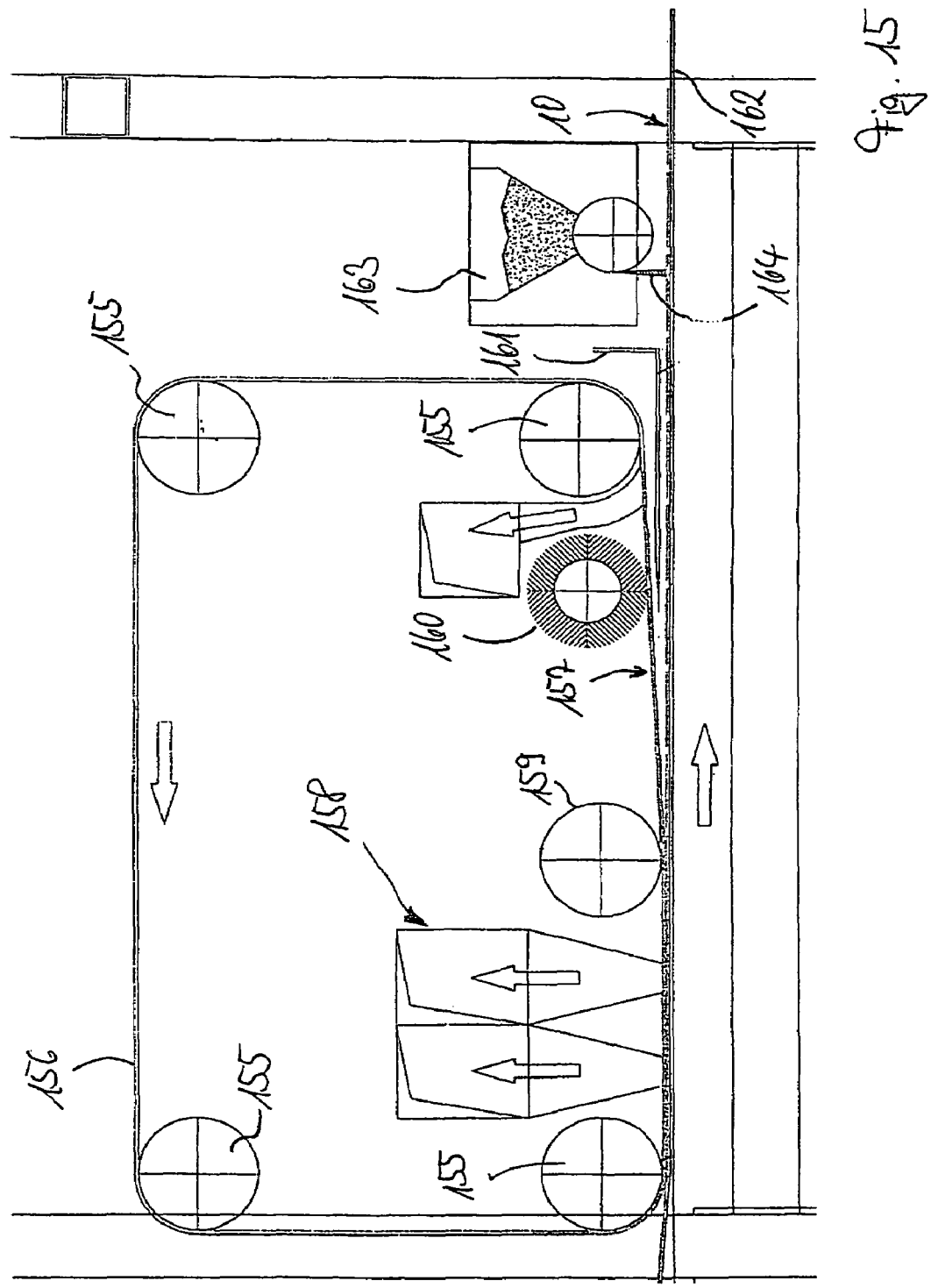
FIG. 15 shows an eleventh apparatus for producing an absorbent sheet.

FIG. 15 shows a further embodiment of an apparatus for producing an absorbent sheet. Likewise, this apparatus is adapted for later installation as a module in an already existing production line. A suction belt 156 extends over four guide rolls 157. The flexible suction belt 156 is preferably laser cut and preferably comprises cutouts 157, which preferably extend transversely to the direction of movement of the suction belt 156. According to an embodiment not shown in greater detail, the suction belt 156 comprises cutouts, which are neither transverse nor parallel to the direction of movement, but rather extend at an angle therewith. Likewise, it is possible that the cutouts 157 have not only parallel extending edges, but also curvatures, i.e., concave or convex shapes. This applies not only to the cutouts in a suction belt 156. Rather, it is possible to find again such a geometry mirror-inverted in the absorbent layer 10 on a first layer 162. This makes it possible to realize with the absorbent layer 10 for different uses not only a rectangular cross section. Rather, such a configuration also permits geometrical shapes, such as, for example, a longitudinal distribution of absorbent material similar to an hourglass, or conical, convex, and other shapes. The suction belt 156 advances on the absorbent layer 10. A suction device 158 removes the material of the absorbent layer 10 adjacent the cutouts 157. The suction device 158 may be constructed in one piece or, however, as shown, from two or more modules. Furthermore, the suction device 158 may completely extend all over a region. Furthermore, it is possible, as shown in the present embodiment, that suction occurs in two separated regions. Downstream of the suction device 158 is a delivery roll 159 that is constructed as a grooved roll. Same creates in cooperation with the upstream guide roll 155 of the suction belt 156 extending in this intermediate section, the possibility of exerting a contact pressure via the suction belt 156 upon the first layer and, thus, likewise upon the absorbent layer 10 arranged therebetween. From the delivery roll 159, the suction belt 156 is raised from the absorbent layer 10 at a small angle by means of a subsequent guide roll 155. A cleaning of the suction belt 156 is performed, for example, as shown, by a brush roll 160. This cleaning device is assisted by a further cleaning, for example, by means of ultrasound and/or suction. In addition, a vibratory plate 161 is associated both to the guide roll and to the brush roll 160. On the one hand, the vibratory plate 161 collects particles that drop from the suction belt 156. On the other hand, when properly suspended, the vibratory plate is in a position to shake at the same time the passing absorbent material on the first layer 162. Downstream of the vibratory plate 161 is a binder feed device 163. A supplied binder 164 is, for example, a binder that melts only at high temperatures.

Figure 16:
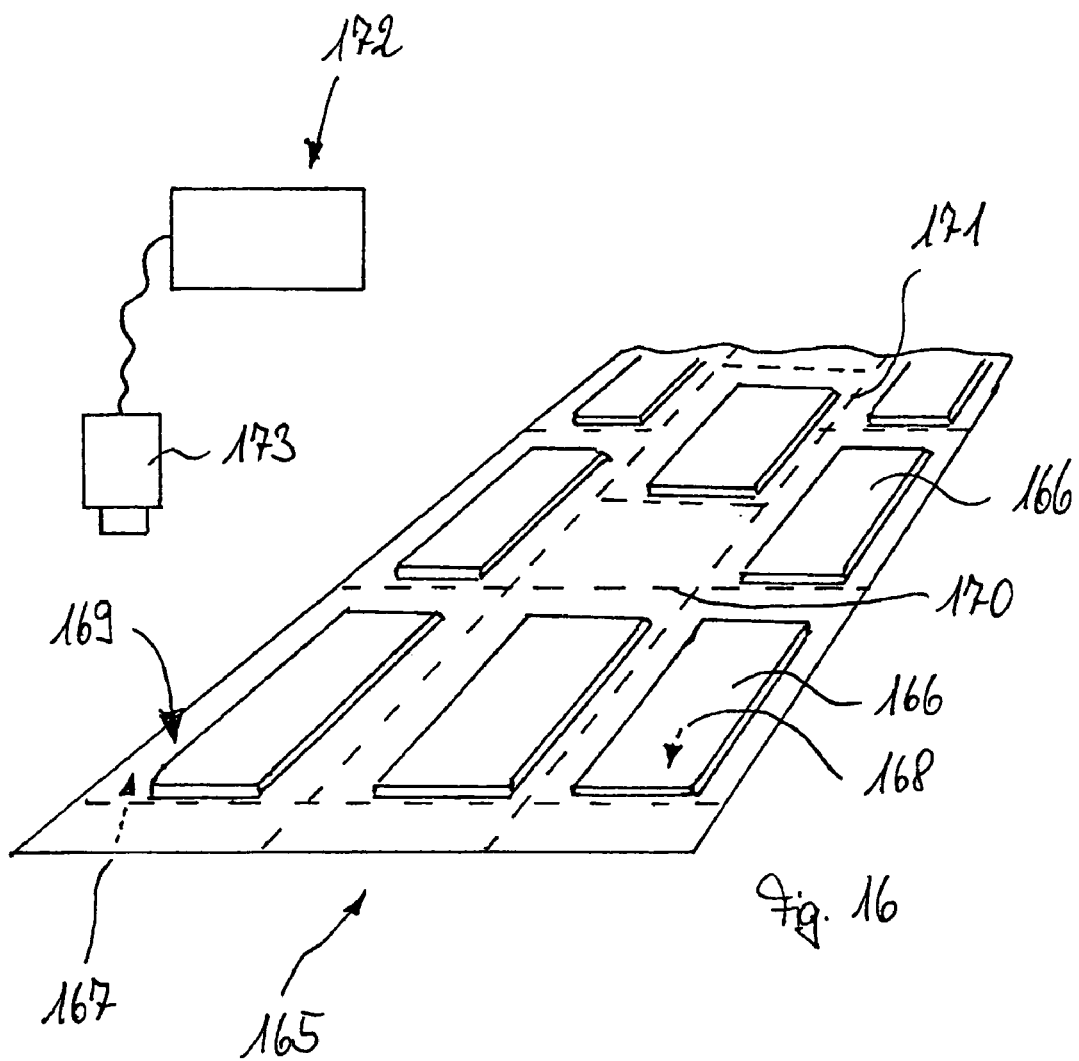
FIG. 16 is a schematic top view of an absorbent sheet with a detection unit.

FIG. 16 is a schematic view of an absorbent sheet 165 as a laminate. The absorbent sheet 165 comprises four absorbent pads 166, preferably of a structure that includes a first layer 167, an interposed absorbent layer 168, and a subsequent layer 169. However, the absorbent pads 166 may also comprise a plurality of such structures, one on top of the other, or they may possess a plurality of absorbent layers 166. This is possible, for example, by folding the absorbent sheet 165, or by a multiple layering. Furthermore, the absorbent pads 166 are provided with both a transverse seal 170 and a longitudinal seal 171. Preferably both the transverse 170 and the longitudinal seal 171 are uninterrupted, i.e., continuous. According to a further development, the transverse seal 170 and the longitudinal seal 171 are individually or jointly interrupted, in part also in defined locations.

Furthermore, FIG. 16 shows a detection unit 172. A sensor 173 is in a position to receive actively or passively a signal from the absorbent sheet 165, which can subsequently be evaluated by the detection unit 172. The received signal is able to provide information, for example, about a cutting plane for both a transverse cut and a longitudinal cut through the absorbent sheet for separating the absorbent pads 166. To this end, the absorbent sheet may comprise markings, such as, for example, grooves, colorations, or the like. It is likewise possible to detect an elevation of the absorbent sheet 165, so that it is possible to obtain information about the location, in which an absorbent layer 168 is present, and about the location, in which it is absent. Furthermore, by illuminating the absorbent sheet 165 and by subsequently performing a light-dark comparison, for example, by means of evaluating images of a CCD camera, it is possible to conclude therefrom the distribution of the absorbent layer 168, and to then obtain corresponding data. According to a further development, the detecting unit is used to detect the applied binder. Moreover, the just described detection unit 172 and different detection possibilities can be used not only for performing cuts through the absorbent sheet 165, but also permit, for example, controlling the position of the absorbent sheet 165 in the course or at the beginning of a further processing step, for example, when depositing it by means of a packaging unit to a form for transportation, or also in a processing line for making an end product. As illustrated, it is possible to arrange the absorbent layers with respect to their transverse seals not only parallel, but also in an alternating fashion.

Furthermore, the invention permits packing the individual absorbent sheets separated from one another to a form for transportation. In a further processing station, this will then make it possible to incorporate the individual absorbent pads in a purposeful manner in or on the end product. For example, in the field of hygiene and incontinence, it will thus be possible to position, for example, in a diaper, the absorbent pads in different ways to conform with the sex-specific location of the genitals.

The proposed method as well as the apparatus and laminates are suitable for processing a large variety of materials. Suitable for both a first and a second layer are, for example, woven materials, as well as paper, nonwovens, in particular airlaid materials, films, or other thin-sheet materials, as well as, single-layer or multilayered material blends. As a powder, one uses alone or in mixtures, for example, an absorbent material, such as SAP, black carbon, zeolite, interspersed with polymeric or other materials. In particular, it is possible to use the laminates that can be produced in accordance with the invention, for example, as absorbent pads, as dispenser pads, as scented pads, as cloth, for example, in the following applications: hygienic articles, such as, for example, sanitary pads, diapers, or absorbent pads for weaning in the case of nursing mothers, incontinence products, such as, absorbent inserts, food processing, for example, in the case of meat pads as well as food packaging, absorber pads, in particular for industrial products, such as oil absorption, absorption of liquids, in particular leakage fluids, furthermore for wash pads for use in washing machines, which include, for example, fragrances and/or detergents, for medical needs, in the case of blood-absorbing materials, such as in operating rooms, in the case of coverings, cleaning materials for operating rooms and surgical garments, for garments, garment cleaning agents as a whole, at the same time also for use in wash cloths, cloths, towels, wipes in housekeeping, for transporting food, for frozen goods, for merchandise that may have fluid losses, as barriers for plugging holes by swelling, in the construction of buildings for protecting against penetration of moisture, in particular also for collecting moisture in ambient air, for example, in the case of dry storage of electronic components or optical devices, both as substrate and as cover.

The invention claimed is:

1. A method for continuously producing a laminate with at least one powder layer, comprising directing a first layer along a longitudinal direction to a second layer; applying powder to the first layer continuously along the longitudinal direction to form several longitudinally extending continuous powder strips adjacent to one another; before applying binder to the first layer and before arranging the second layer on the powder layer and the first layer, removing portions of each of the continuously applied powder strips from the first layer, thereby producing powder layers that are separated from one another and which are arranged one after another in the longitudinal direction; applying binder to the first layer at least in strips between the separated powder layers in areas that have been cleared of powder; and directing the second layer onto the powder layer and the first layer and forming a transversely extending seal between the first and second layers along the strips of binder.

2. The method of claim 1, comprising applying to the first layer an additional binder in the longitudinal direction for producing a longitudinal seal.

3. The method of claim 2, wherein the longitudinal seal of the laminate is continuously produced.

4. The method of claim 1, wherein the binder is arranged at least in part discontinuously.

5. The method of claim 1, wherein at least one portion of the seal is mechanically produced, with the binder producing a mechanically acting bond between the first and the second layer.

6. The method of claim 1, wherein an adhesive is applied at least in part to the second layer, which is subsequently supplied to the first layer carrying the powder layer.

7. The method of claim 6, including cutting the first layer and the second layer only after having totally sealed the powder layer.

8. The method of claim 7, wherein the individual, separated and sealed powder layers are deposited, and individual laminates are supplied to further processing.

9. The method of claim 7, wherein completely sealed and spaced powder layers are stored in a coherent manner and subsequently supplied to further processing, in which the sealed powder layers are separated from one another at least in part.

10. The method of claim 1, wherein, as an ingredient of the powder layer, at least one material is used that is in a position to influence at least a direct environment of the laminate.

11. The method of claim 1, wherein, as an ingredient of the powder layer, at least one absorbent material is used, and the laminate is produced as an absorbent sheet.

12. The method of claim 1, wherein, as an ingredient for the powder layer at least one odor-influencing material is used.

13. The method of claim 1, wherein, as an ingredient of the powder layer at least one detergent is used.

14. The method of claim 1, wherein, with the powder layer, a material of a different geometric configuration is applied to the first layer.

* * * * *